(12) United States Patent
Gowans et al.

(10) Patent No.: US 11,970,555 B2
(45) Date of Patent: Apr. 30, 2024

(54) BICYCLIC PEPTIDE LIGANDS SPECIFIC FOR TRANSFERRIN RECEPTOR 1 (TFR1)

(71) Applicant: BicycleTx Limited, Cambridge (GB)

(72) Inventors: Ellen Gowans, Cambridge (GB); Gemma Elizabeth Mudd, Cambridge (GB); Michael Rigby, Cambridge (GB); Punit Seth, Carlsbad, CA (US); Michael Skynner, Cambridge (GB); Steven Stanway, Cambridge (GB); Liudvikas Urbonas, Cambridge (GB); Katerine Van Rietschoten, Cambridge (GB)

(73) Assignee: BicycleTx Limited, Cambridge (GB)

( * ) Notice: Subject to any disclaimer, the term of this patent is extended or adjusted under 35 U.S.C. 154(b) by 65 days.

(21) Appl. No.: 17/454,665

(22) Filed: Nov. 12, 2021

(65) Prior Publication Data
US 2022/0194988 A1   Jun. 23, 2022

Related U.S. Application Data

(60) Provisional application No. 63/261,820, filed on Sep. 29, 2021.

(30) Foreign Application Priority Data

Nov. 13, 2020 (GB) .................................. 2017927
May 14, 2021 (GB) .................................. 2106903

(51) Int. Cl.
| | |
|---|---|
| C07K 7/64 | (2006.01) |
| A61K 47/55 | (2017.01) |
| A61K 47/64 | (2017.01) |
| C07K 1/107 | (2006.01) |

(52) U.S. Cl.
CPC .............. *C07K 7/64* (2013.01); *A61K 47/55* (2017.08); *A61K 47/64* (2017.08); *C07K 1/1075* (2013.01)

(58) Field of Classification Search
None
See application file for complete search history.

(56) References Cited

U.S. PATENT DOCUMENTS

| 10,857,196 B2 * | 12/2020 | Beswick | A61K 38/005 |
| 2021/0101932 A1 * | 4/2021 | Chen | A61P 35/00 |
| 2022/0281918 A1 * | 9/2022 | Van Rietschoten | C07K 7/64 |

FOREIGN PATENT DOCUMENTS

| CN | 104650186 A | 5/2015 |
| WO | WO-2016077840 A2 | 5/2016 |
| WO | WO-2018197509 A1 | 11/2018 |
| WO | WO-2018197893 A1 | 11/2018 |
| WO | WO-2019162682 A1 | 8/2019 |
| WO | WO-2020084305 A1 | 4/2020 |
| WO | WO-2022101633 A1 | 5/2022 |

OTHER PUBLICATIONS

Lowe, Derek; "Not alphafold's fault." blog in the Pipeline, issue of Sep. 7, 2022.*
Guo, Haiwei H. et al; "Protein tolerance to random amino acid change." PNAS (2004) 101(25) p. 9205-9210.*
Yampolsky, Lev Y. and Stoltzfus, Arlin; "The exchangeability of amino acids in proteins." Genetics (2005) 170 p. 1459-1472.*
Kale et al., "Cyclization of peptides with two chemical bridges affords large scaffold diversities," Nature Chemistry 2018; 10(7):715-723.
Deyle et al., "Phage Selection of Cyclic Peptides for Application in Research and Drug Development," Accounts of Chmical Research 2017;50(8):1866-1874.
Ali et al., "Transferrin Trojan Horses as a Rational Approach for the Biological Delivery of Therapeutic Peptide Domains," The Journal of Biological Chemistry 1999;274(34):24066-24073.
Staquicini et al., "Systemic combinatorial peptide selection yields a non-canonical iron-mimicry mechanism for targeting tumors in a mouse model of human glioblastoma," The Journal of Clinical Investigation 2011;121(1):161-173.
PCT International Search Report and Written Opinion from PCT/GB2021/052927, dated Feb. 22, 2022.

* cited by examiner

*Primary Examiner* — Fred H Reynolds
(74) *Attorney, Agent, or Firm* — Dechert LLP; Andrea L. C. Reid; Gang Wang

(57) ABSTRACT

The present invention relates to polypeptides which are covalently bound to molecular scaffolds such that two or more peptide loops are subtended between attachment points to the scaffold. In particular, the invention describes peptides which bind to TfR1. The invention also relates to multimeric binding complexes which comprise at least two of said bicyclic peptide ligands. The invention also includes pharmaceutical compositions comprising said peptide ligands and multimeric binding complexes and the use of said peptide ligands, and multimeric binding complexes and pharmaceutical compositions in preventing, suppressing or treating a disease or disorder through TfR1 mediated delivery of a therapeutic agent.

20 Claims, 8 Drawing Sheets

Specification includes a Sequence Listing.

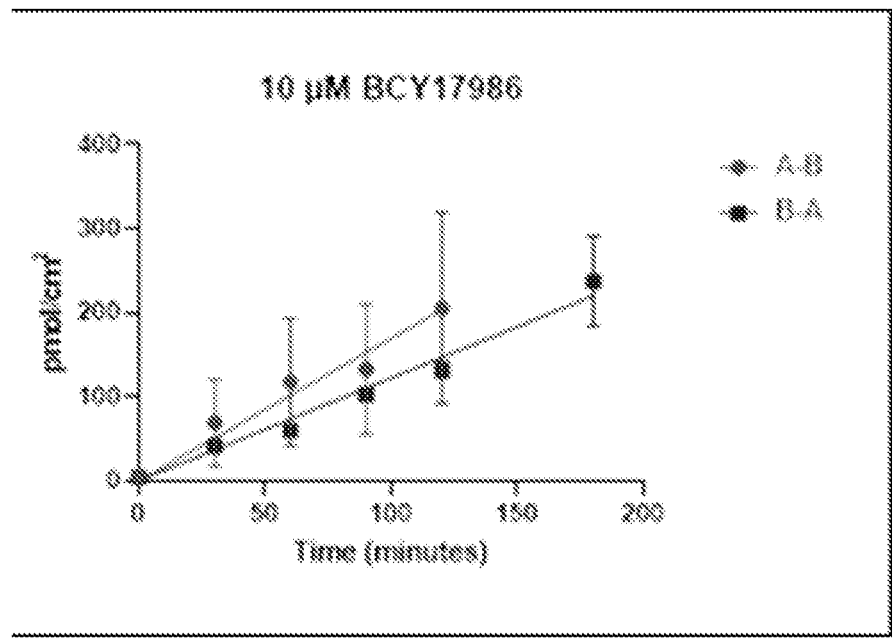
FIG. 1 (ctd)

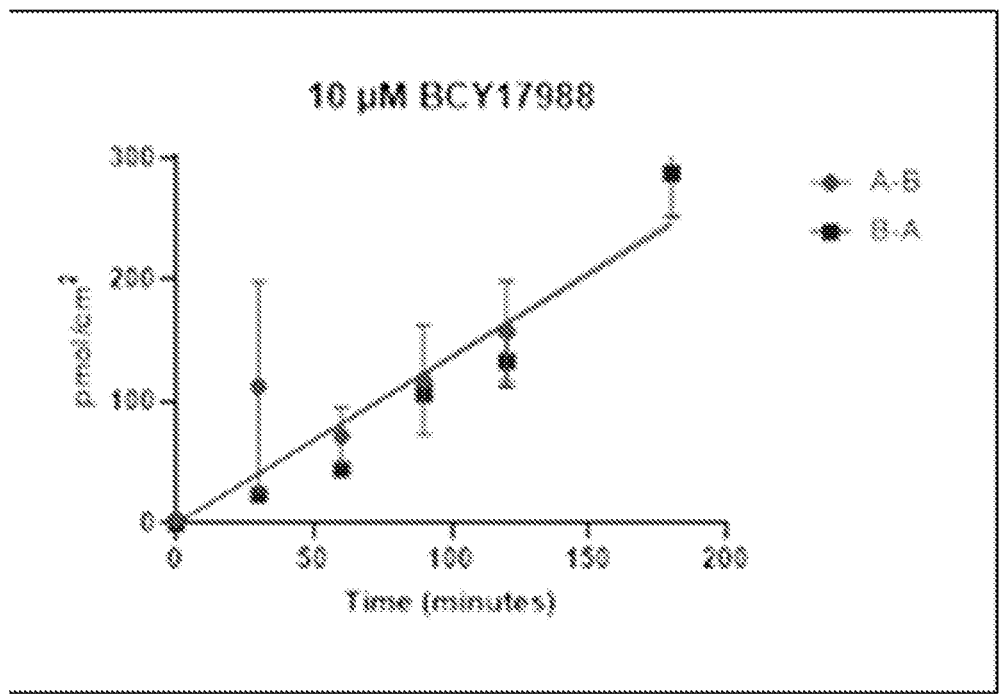
FIG. 2 (ctd)

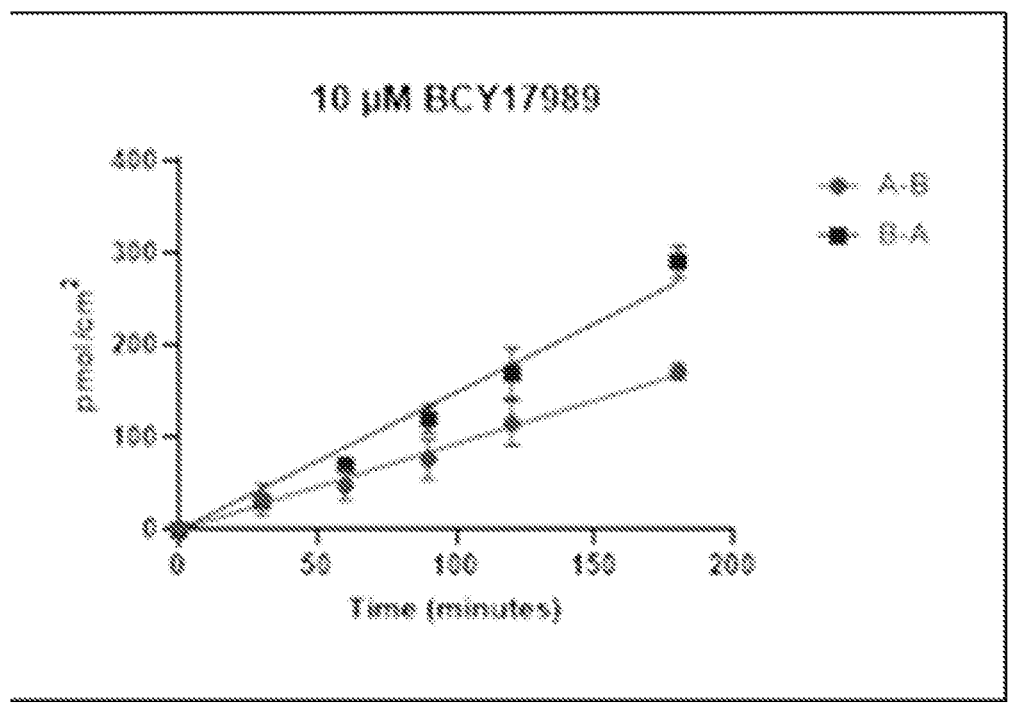
FIG. 3 (ctd)

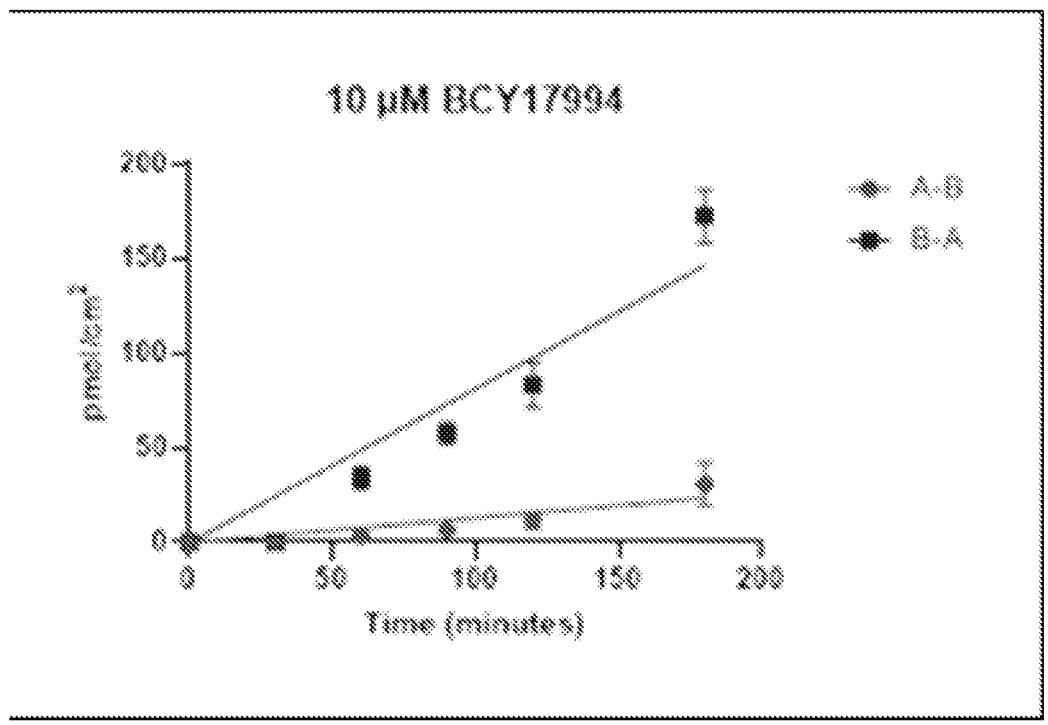
FIG. 4 (ctd)

BICYCLIC PEPTIDE LIGANDS SPECIFIC FOR TRANSFERRIN RECEPTOR 1 (TFR1)

CROSS-REFERENCE TO RELATED APPLICATIONS

This application claims priority under 35 U.S.C. § 119 to U.S. Provisional Application No. 63/261,820, filed Sep. 29, 2021, United Kingdom Application No. GB2106903.4, filed May 14, 2021, and United Kingdom Application No. GB2017927.1, filed Nov. 13, 2020, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 22, 2022, is named Bicycle_187252_SL.txt and is 16.7 kilobytes in size.

FIELD OF THE INVENTION

The present invention relates to polypeptides which are covalently bound to molecular scaffolds such that two or more peptide loops are subtended between attachment points to the scaffold. In particular, the invention describes peptides which bind to TfR1. The invention also relates to multimeric binding complexes which comprise at least two of said bicyclic peptide ligands. The invention also includes pharmaceutical compositions comprising said peptide ligands and multimeric binding complexes and the use of said peptide ligands, and multimeric binding complexes and pharmaceutical compositions in preventing, suppressing or treating a disease or disorder through TfR1 mediated delivery of a therapeutic agent.

BACKGROUND OF THE INVENTION

Cyclic peptides are able to bind with high affinity and specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat. Rev. Drug. Discov. 7(7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 $Å^2$; Wu et al. (2007), Science 330, 1066-71), a cyclic peptide with the Arg-Gly-Asp motif binding to integrin αVb3 (355 $Å^2$) (Xiong et al. (2002), Science 296(5565), 151-5) or the cyclic peptide inhibitor upain-1 binding to urokinase-type plasminogen activator (603 $Å^2$; Zhao et al. (2007), J. Struct. Biol. 160(1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8 (MMP-8) which lost its selectivity over other MMPs when its ring was opened (Cherney et al. (1998), J. Med. Chem. 41(11), 1749-51). The favourable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example 1,1',1"-(1,3,5-triazinane-1,3,5-triyl)triprop-2-en-1-one (TATA) (Heinis et al. (2014) Angewandte Chemie, International Edition 53(6) 1602-1606).

Phage display-based combinatorial approaches have been developed to generate and screen large libraries of bicyclic peptides to targets of interest (Heinis et al. (2009), Nat. Chem. Biol. 5(7), 502-7 and WO 2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule scaffold.

SUMMARY OF THE INVENTION

According to a first aspect of the invention, there is provided a peptide ligand specific for transferrin receptor 1 (TfR1) comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a multimeric binding complex which comprises at least two bicyclic peptide ligands, wherein said peptide ligands may be the same or different, each of which comprises a peptide ligand specific for transferrin receptor 1 (TfR1) comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a yet further aspect of the invention, there is provided a pharmaceutical composition comprising a peptide ligand or multimeric binding complex as defined herein in combination with one or more pharmaceutically acceptable excipients.

According to a further aspect of the invention, there is provided a peptide ligand, or multimeric binding complex or pharmaceutical composition as defined herein for use in preventing, suppressing or treating a disease or disorder through TfR1 mediated delivery of a therapeutic agent.

DETAILED DESCRIPTION OF THE INVENTION

Figure 1:
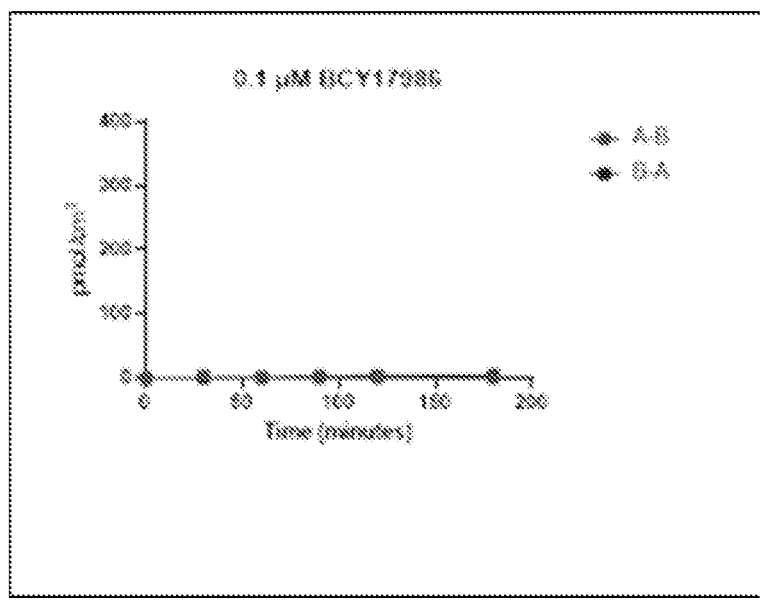
FIG. 1: Results of transcytosis assay with BCY17986 in primary cultures of human proximal convoluted cells.
Figure 1:
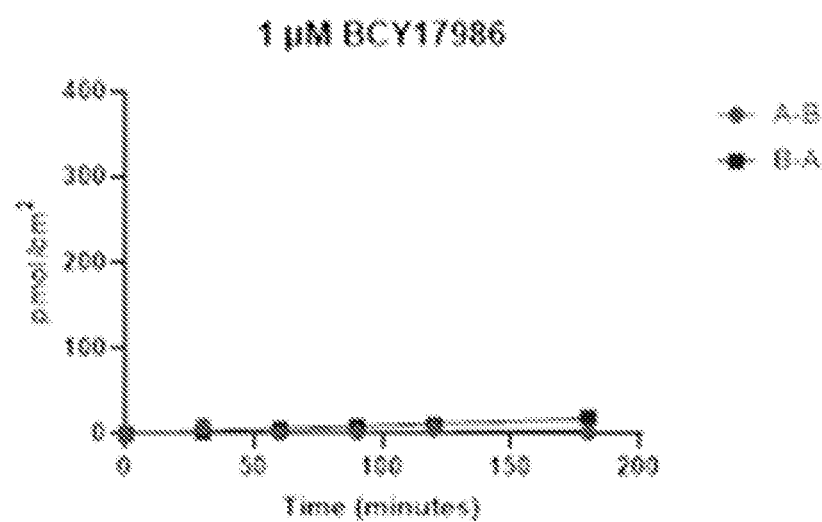

It will be appreciated that the present invention relates to both "monomeric" bicyclic peptides, i.e. those which contain a single (monomeric) bicyclic peptide ligand and "multimeric" bicyclic peptides, i.e. 'those which contain more than one bicyclic peptide (such as 2, 3 or 4) conjugated via one or more linkers.

Monomeric Bicyclic Peptide Ligands

According to a first aspect of the invention, there is provided a peptide ligand specific for transferrin receptor 1 (TfR1) comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

In one embodiment, said reactive groups comprise cysteine residues.

It will be appreciated that the term "specific for TfR1" refers to the ability of the peptide ligand to bind to transferrin receptor 1 (TfR1). It will also be appreciated that the peptide ligand will have a differing affect upon TfR1 depending on the precise epitope of binding. For example, the affect will either be inhibitory (i.e. the peptide ligand impedes/inhibits the binding of transferrin to TfR1) or non-inhibitory (i.e. the peptide ligand does not impede/inhibit the binding of transferrin to TfR1.

Inhibitory Peptide Ligands

In one embodiment, the peptide ligand is specific for TfR1 and binds to TfR1 in a manner which impedes/inhibits the binding of transferrin to TfR1.

In a further embodiment, said loop sequences comprise 2, 3, 6, 8 or 9 amino acids.

In one embodiment, said loop sequences comprise three cysteine residues separated by two loop sequences the first of which consists of 2 amino acids and the second of which consists of 9 amino acids.

In one embodiment, said loop sequences comprise three cysteine residues separated by two loop sequences both of which consist of 6 amino acids.

In one embodiment, said loop sequences comprise three cysteine residues separated by two loop sequences the first of which consists of 3 amino acids and the second of which consists of 8 amino acids.

In one embodiment, the peptide ligand comprises an amino acid sequence of:

$C_i$ALC$_{ii}$NDWTLPWHHC$_{iii}$; (SEQ ID NO: 1)

$C_i$REFFDTC$_{ii}$GLAFIEC$_{iii}$; (SEQ ID NO: 2)
and $C_i$LEAC$_{ii}$YDGVYWYSC$_{iii}$; (SEQ ID NO: 3)

wherein $C_i$, $C_{ii}$ and $C_{iii}$ represent first, second and third cysteine residues, respectively, or a pharmaceutically acceptable salt thereof.

In a further embodiment, the molecular scaffold is 1,1',1"-(1,3,5-triazinane-1,3,5-triyl)triprop-2-en-1-one (TATA) and the peptide ligand comprises N- and/or C-terminal additions and is selected from:

A-(SEQ ID NO: 1)-A (herein referred to as BCY12455);
A-(SEQ ID NO: 1)-A-[Sar$_6$]-[K-Fl] (herein referred to as BCY12652);
A-(SEQ ID NO: 2)-A (herein referred to as BCY12452);
A-(SEQ ID NO: 2)-A-[Sar$_6$]-[K-Fl] (herein referred to as BCY12650);
A-(SEQ ID NO: 3)-A (herein referred to as BCY12454); and
A-(SEQ ID NO: 3)-A-[Sar$_6$]-[K-Fl] (herein referred to as BCY12651).

wherein Sar represents sarcosine and Fl represents fluorescein.

For the purpose of this description, inhibitory bicyclic peptides are assumed to be cyclised with TATA and yielding a tri-substituted structure. However, as will be clear from the descriptions of the invention presented herein, cyclisation may be performed with any suitable molecular scaffold which forms covalent bonds with the reactive groups of the polypeptide such that at least two polypeptide loops are formed. Cyclisation occurs on $C_i$, $C_{ii}$, and $C_{iii}$.

Non-Inhibitory Peptide Ligands

In one embodiment, the peptide ligand is specific for TfR1 and binds to TfR1 in a manner which does not inhibit/impede the binding of transferrin to TfR1. In a further embodiment, said loop sequences comprise 3 or 7 amino acids.

In one embodiment, said loop sequences comprise three cysteine residues separated by two loop sequences the first of which consists of 7 amino acids and the second of which consists of 3 amino acids.

In one embodiment, the peptide ligand comprises an amino acid sequence of:

$C_i$SADDWLGC$_{ii}$ISWC$_{iii}$; (SEQ ID NO: 4)

$C_i$SSDAYLGC$_{ii}$ISWC$_{iii}$; (SEQ ID NO: 5)

$C_i$PPDAHLGC$_{ii}$ISWC$_{iii}$; (SEQ ID NO: 6)

$C_i$PQDAYLGC$_{ii}$ISWC$_{iii}$; (SEQ ID NO: 7)

$C_i$PPDSWQGC$_{ii}$ISYC$_{iii}$; (SEQ ID NO: 8)

$C_i$SPDAHLGC$_{ii}$ISYC$_{iii}$ (SEQ ID NO: 9)
(herein referred to as BCY15935);

$C_i$PGDAHLGC$_{ii}$ISYC$_{iii}$; (SEQ ID NO: 10)

$C_i$PPDSHLGC$_{ii}$ISYC$_{iii}$; (SEQ ID NO: 11)

$C_i$SADDWLGC$_{ii}$ISYC$_{iii}$; (SEQ ID NO: 12)

$C_i$P[HyP]DAYLGC$_{ii}$[tBuGly]SYC$_{iii}$; (SEQ ID NO: 13)

$C_i$P[HyP]DAYLGC$_{ii}$ISYC$_{iii}$; (SEQ ID NO: 14)

$C_i$S[HyP]DAHLGC$_{ii}$ISYC$_{iii}$; (SEQ ID NO: 15)

$C_i$P[Aib]DAHLGC$_{ii}$[tBuGly]SYC$_{iii}$; (SEQ ID NO: 16)

| | |
|---|---|
| $C_iPPDAHLGC_{ii}ISYC_{iii}$; | (SEQ ID NO: 17) |
| $C_iP[Aib]DAYLGC_{ii}[tBuGly]SYC_{iii}$; | (SEQ ID NO: 18) |
| $C_iSADAHLGC_{ii}ISYC_{iii}$; | (SEQ ID NO: 19) |
| $C_iS[Aib]DAHLGC_{ii}[tBuGly]SYC_{iii}$; | (SEQ ID NO: 20) |
| $C_iSPDAHLGC_{ii}[EPA]SYC_{iii}$; | (SEQ ID NO: 21) |
| $C_iPPDAYLGC_{ii}[tBuGly]SYC_{iii}$; | (SEQ ID NO: 22) |
| $C_iS[Aib]DAYLGC_{ii}[tBuGly]SYC_{iii}$; | (SEQ ID NO: 23) |
| $C_iAPDAHLGC_{ii}ISYC_{iii}$; | (SEQ ID NO: 24) |
| $C_iP[Aib]DAHLGC_{ii}ISYC_{iii}$; | (SEQ ID NO: 25) |
| $C_iSPDAYLGC_{ii}[tBuGly]SYC_{iii}$; | (SEQ ID NO: 26) |
| $C_iSPDAHLGC_{ii}[tBuGly]SYC_{iii}$; | (SEQ ID NO: 27) |
| $C_iPNDAHLGC_{ii}ISYC_{iii}$; | (SEQ ID NO: 28) |
| $C_iPIDAHLGC_{ii}ISYC_{iii}$; | (SEQ ID NO: 29) |
| $C_iSPDAYLGC_{ii}ISYC_{iii}$; | (SEQ ID NO: 30) |
| $C_iPPDAYLGC_{ii}ISYC_{iii}$; | (SEQ ID NO: 31) |
| $C_iS[Aib]DAHLGC_{ii}ISYC_{iii}$; | (SEQ ID NO: 32) |
| $C_iSPDAHLGC_{ii}[Chg]SYC_{iii}$; | (SEQ ID NO: 33) |
| $C_iAPDAHLGC_{ii}ISYC_{iii}$; | (SEQ ID NO: 34) |
| $C_iYLPDW[tBuAla]C_{ii}GDEYC_{iii}$; | (SEQ ID NO: 35) |
| $C_iSPDAHLGC_{ii}IS[2Nal]C_{iii}$; | (SEQ ID NO: 36) |
| $C_iSPDAHLGC_{ii}IS[3tBuTyr]C_{iii}$; | (SEQ ID NO: 37) |
| $C_iSPD[Aib]HLGC_{ii}ISYC_{iii}$; | (SEQ ID NO: 38) |
| $C_iSPDAHLGC_{ii}IS[1Nal]C_{iii}$; | (SEQ ID NO: 39) |
| $C_iSPDAH[tBuAla]GC_{ii}ISYC_{iii}$; | (SEQ ID NO: 40) |
| $C_iSPDAH[Cba]GC_{ii}ISYC_{iii}$; | (SEQ ID NO: 41) |
| $C_iSPDAHLGC_{ii}ISWC_{iii}$; | (SEQ ID NO: 42) |
| $C_iSPD[Abu]HLGC_{ii}ISYC_{iii}$; | (SEQ ID NO: 43) |
| $C_iS[Aze]DAHLGC_{ii}ISYC_{iii}$; | (SEQ ID NO: 44) |
| $C_iSPDDHLGC_{ii}ISYC_{iii}$; | (SEQ ID NO: 45) |
| $C_iSPDSHLGC_{ii}ISYC_{iii}$; | (SEQ ID NO: 46) |
| $C_iSPDAH[Abu]GC_{ii}ISYC_{iii}$; | (SEQ ID NO: 47) |
| $C_iSPDAHLGC_{ii}IS[4Pal]C_{iii}$; | (SEQ ID NO: 48) |
| $C_iP[dA]DAHLGC_{ii}ISYC_{iii}$; | (SEQ ID NO: 49) |
| $C_iSPDAYLGC_{ii}[tBuAla]SYC_{iii}$; | (SEQ ID NO: 50) |
| $C_iSPDAHLGC_{ii}[C5g]SYC_{iii}$; | (SEQ ID NO: 51) |
| $C_iSPDAHLGC_{ii}[Cbg]SYC_{iii}$; | (SEQ ID NO: 52) |
| $C_iSPDAHL[dA]C_{ii}ISYC_{iii}$; | (SEQ ID NO: 53) |
| $C_iSPDAH[Aib]GC_{ii}ISYC_{iii}$; | (SEQ ID NO: 54) |
| $C_iSPDAHLGC_{ii}[Cpg]SYC_{iii}$; | (SEQ ID NO: 55) |
| $C_iSPDAHLGC_{ii}[B-MeIle]SYC_{iii}$; | (SEQ ID NO: 56) |
| $C_iSADAHLGC_{ii}ISYC_{iii}$; | (SEQ ID NO: 57) |
| $C_iSPAAHLGC_{ii}ISYC_{iii}$; | (SEQ ID NO: 58) |
| $C_iSPDAALGC_{ii}ISYC_{iii}$; | (SEQ ID NO: 59) |
| $C_iSPDAHAGC_{ii}ISYC_{iii}$; | (SEQ ID NO: 60) |
| $C_iSPDAHLAC_{ii}ISYC_{iii}$; | (SEQ ID NO: 61) |
| $C_iSPDAHLGC_{ii}ASYC_{iii}$; | (SEQ ID NO: 62) |
| $C_iSPDAHLGC_{ii}AYC_{iii}$; | (SEQ ID NO: 63) |
| $C_iSPDAHLGC_{ii}SAC_{iii}$; | (SEQ ID NO: 64) |
| $C_i[K(N_3)]APDAHLGC_{ii}ISYC_{iii}$; | (SEQ ID NO: 65) |
| $C_iS[K(N_3)]ADAHLGC_{ii}ISYC_{iii}$; and | (SEQ ID NO: 66) |
| $C_iSPD[K(N_3)]HLGC_{ii}ISYC_{iii}$; | (SEQ ID NO: 67) | wherein Abu represents aminobutyric acid, Aib represents aminoisobutyric acid, Aze represents azetidine, B-MeIle represents beta-methyl isoleucine, C5g represents cyclopentyl glycine, Cba represents β-cyclobutylalanine, Cbg represents cyclobutyl glycine, Chg represents cyclohexyl glycine, Cpg represents cyclopropryl glycine, EPA represents 2-amino-3-ethyl-pentanoic acid, HyP represents trans-4-hydroxy-L-proline, [K(N$_3$)] represents 6-azido lysine, 1Nal represents 1-naphthylalanine, 2Nal represents 2-naphthylalanine, 4Pal represents 4-pyridylalanine, tBuAla represents t-butyl-alanine, tBuGly represents t-butyl-glycine, 3tBuTyr represents 3-t-Butyl-Tyrosine, and $C_i$, $C_{ii}$ and $C_{iii}$ represent first, second and third cysteine residues, respectively, or a pharmaceutically acceptable salt thereof.

In a further embodiment the peptide ligand comprises an amino acid sequence of:

$C_i$SADDWLG$C_{ii}$ISW$C_{iii}$; (SEQ ID NO: 4)

$C_i$SSDAYLG$C_{ii}$ISW$C_{iii}$; (SEQ ID NO: 5)

$C_i$PPDAHLG$C_{ii}$ISW$C_{iii}$; (SEQ ID NO: 6)

$C_i$PQDAYLG$C_{ii}$ISW$C_{iii}$; (SEQ ID NO: 7)

$C_i$PPDSWQG$C_{ii}$ISY$C_{iii}$; (SEQ ID NO: 8)

$C_i$SPDAHLG$C_{ii}$ISY$C_{iii}$; (SEQ ID NO: 9)

$C_i$PGDAHLG$C_{ii}$ISY$C_{iii}$; (SEQ ID NO: 10)

$C_i$PPDSHLG$C_{ii}$ISY$C_{iii}$; and (SEQ ID NO: 11)

$C_i$SADDWLG$C_{ii}$ISY$C_{iii}$; (SEQ ID NO: 12)

wherein $C_i$, $C_{ii}$ and $C_{iii}$ represent first, second and third cysteine residues, respectively, or a pharmaceutically acceptable salt thereof.

In a further embodiment, the molecular scaffold is 1,1',1''-(1,3,5-triazinane-1,3,5-triyl)tris(2-bromoethanone) (TATB) and the peptide ligand comprises N- and/or C-terminal additions and is selected from:

A-(SEQ ID NO: 4)-A (herein referred to as BCY13983);

A-(SEQ ID NO: 4)-A-[Sar$_6$]-[K-FI] (herein referred to as BCY14474);

A-(SEQ ID NO: 5)-A (herein referred to as BCY13986);

A-(SEQ ID NO: 5)-A-[Sar$_6$]-[K-FI] (herein referred to as BCY14475);

A-(SEQ ID NO: 6)-A (herein referred to as BCY15466);

Ac-(SEQ ID NO: 6) (herein referred to as BCY15889);

A-(SEQ ID NO: 7)-A (herein referred to as BCY15467);

Ac-(SEQ ID NO: 7) (herein referred to as BCY15890);

A-(SEQ ID NO: 8)-A (herein referred to as BCY13989);

A-(SEQ ID NO: 8)-A-[Sar$_6$]-[K-FI] (herein referred to as BCY14476);

A-(SEQ ID NO: 9)-A (herein referred to as BCY15468);

A-(SEQ ID NO: 9)-A-[Sar$_6$]-[K-FI] (herein referred to as BCY15768);

(SEQ ID NO: 9)-[Sar$_6$]-[K-FI] (herein referred to as BCY15934);

Ac-(SEQ ID NO: 9)-A-[Sar$_6$]-[K-FI] (herein referred to as BCY15937);

Ac-(SEQ ID NO: 9)-[Sar$_6$]-[K-FI] (herein referred to as BCY15938);

[FI]G[Sar$_5$]-A-(SEQ ID NO: 9)-A (herein referred to as BCY15940);

N[1Nal]N-(SEQ ID NO: 9) (herein referred to as BCY18030);

Ac-(SEQ ID NO: 9)-E[Pip]W (herein referred to as BCY18039);

Ac-(SEQ ID NO: 9)-EPW (herein referred to as BCY17994);

NWN-(SEQ ID NO: 9) (herein referred to as BCY18029);

NWN-(SEQ ID NO: 9)-A (herein referred to as BCY17109);

Ac-(SEQ ID NO: 9)-E[Aze]W (herein referred to as BCY18037);

Ac-NWN-(SEQ ID NO: 9) (herein referred to as BCY17992);

Ac-(SEQ ID NO: 9)-E[dP]W (herein referred to as BCY18038);

Ac-N[1Nal]N-(SEQ ID NO: 9) (herein referred to as BCY18034);

N[dW]N-(SEQ ID NO: 9) (herein referred to as BCY18031);

Ac-N[dW]N-(SEQ ID NO: 9) (herein referred to as BCY18035);

-continued

HWM-(SEQ ID NO: 9)-A (herein referred to as BCY17110);

A-(SEQ ID NO: 9)-PHP (herein referred to as BCY17115);

A-(SEQ ID NO: 9)-EPW (herein referred to as BCY17114);

NEV-(SEQ ID NO: 9)-A (herein referred to as BCY17112);

A-(SEQ ID NO: 9)-PIVH (herein referred to as BCY17120);

Ac-(SEQ ID NO: 9) (herein referred to as BCY15891);

HTS-(SEQ ID NO: 9)-A (herein referred to as BCY17111);

Ac-N[NMeTrp]N-(SEQ ID NO: 9) (herein referred to as BCY18036);

N[NMeTrp]N-(SEQ ID NO: 9) (herein referred to as BCY18032);

Ac-A-(SEQ ID NO: 9)-A (herein referred to as BCY15939);

A-(SEQ ID NO: 9)-EHQE (herein referred to as BCY17119);

ESF-(SEQ ID NO: 9)-A (herein referred to as BCY17113);

NWN-(SEQ ID NO: 9)-[K(N3)] (herein referred to as BCY17870);

Ac-NWN-(SEQ ID NO: 9)-[K(N3)] (herein referred to as BCY17871);

[AzPro]-NWN-(SEQ ID NO: 9) (herein referred to as BCY17872);

Ac-(SEQ ID NO: 9)-EPW-[K($N_3$)] (herein referred to as BCY17873);

[AzPro]-(SEQ ID NO: 9)-EPW (herein referred to as BCY17874);

Ac-(SEQ ID NO: 9)-[K($N_3$)] (herein referred to as BCY17868);

[AzPro]-(SEQ ID NO: 9) (herein referred to as BCY17869);

Ac-N[dY]N-(SEQ ID NO: 9)-[K($N_3$)] (herein referred to as BCY17882);

Ac-(SEQ ID NO: 9)-E-[dP]-W-[K($N_3$)] (herein referred to as BCY17890);

Ac-(SEQ ID NO: 9)-E-[Aze]-W-[K($N_3$)] (herein referred to as BCY17892);

Ac-(SEQ ID NO: 9)-E-[Pip]-W-[K($N_3$)] (herein referred to as BCY17894);

Ac-(SEQ ID NO: 9)-[K($N_3$)(PYA-maleimide] (herein referred to as BCY17906);

Ac-(SEQ ID NO: 9)-EPW-[Peg$_{10}$]-[K($N_3$)] (herein referred to as BCY19405);

Ac-(SEQ ID NO: 9)-EPW-[Peg$_{24}$]-[K($N_3$)] (herein referred to as BCY19406);

Ac-(SEQ ID NO: 9)-EPWGGSGGS-[K($N_3$)] (herein referred to as BCY19407);

A-(SEQ ID NO: 10)-A (herein referred to as BCY15469);

Ac-(SEQ ID NO: 10) (herein referred to as BCY15892);

A-(SEQ ID NO: 11)-A (herein referred to as BCY15470);

Ac-(SEQ ID NO: 11) (herein referred to as BCY15893);

A-(SEQ ID NO: 12)-A (herein referred to as BCY15471);

Ac-(SEQ ID NO: 12) (herein referred to as BCY15894);

Ac-(SEQ ID NO: 13) (herein referred to as BCY17991);

Ac-(SEQ ID NO: 13)-EPW (herein referred to as BCY17995);

Ac-NWN-(SEQ ID NO: 13) (herein referred to as BCY17993);

NWN-(SEQ ID NO: 13) (herein referred to as BCY18033);

A-(SEQ ID NO: 13)-A (herein referred to as BCY16754);

Ac-(SEQ ID NO: 13)-[K($N_3$)] (herein referred to as BCY17896);

Ac-NWN-(SEQ ID NO: 13)-[K($N_3$)] (herein referred to as BCY17899);

Ac-(SEQ ID NO: 13)-EPW-[K($N_3$)] (herein referred to as BCY17901);

-continued

Ac-(SEQ ID NO: 14) (herein referred to as BCY17990);

Ac-(SEQ ID NO: 14)-[K(N$_3$)] (herein referred to as BCY17875);

[AzPro]-(SEQ ID NO: 14) (herein referred to as BCY17876);

Ac-(SEQ ID NO: 15) (herein referred to as BCY17989);

A-(SEQ ID NO: 15)-A (herein referred to as BCY16047);

Ac-(SEQ ID NO: 15)-[K(N$_3$)] (herein referred to as BCY17877);

[AzPro]-(SEQ ID NO: 15) (herein referred to as BCY17878);

A-(SEQ ID NO: 16)-A (herein referred to as BCY16962);

TYMN-(SEQ ID NO: 17)-A (herein referred to as BCY17117);

A-(SEQ ID NO: 17)-A (herein referred to as BCY16048);

A-(SEQ ID NO: 18)-A (herein referred to as BCY16963);

Ac-(SEQ ID NO: 19) (herein referred to as BCY17987);

A-(SEQ ID NO: 20)-A (herein referred to as BCY16753);

A-(SEQ ID NO: 21)-A (herein referred to as BCY16046);

A-(SEQ ID NO: 22)-A (herein referred to as BCY16964);

A-(SEQ ID NO: 23)-A (herein referred to as BCY16965);

Ac-(SEQ ID NO: 24) (herein referred to as BCY17986);

A-(SEQ ID NO: 25)-A (herein referred to as BCY16550);

A-(SEQ ID NO: 26)-A (herein referred to as BCY16966);

A-(SEQ ID NO: 27)-A (herein referred to as BCY16051);

IDSN-(SEQ ID NO: 28)-A (herein referred to as BCY17118);

WGKS-(SEQ ID NO: 29)-A (herein referred to as BCY17116);

A-(SEQ ID NO: 30)-A (herein referred to as BCY16053);

A-(SEQ ID NO: 31)-A (herein referred to as BCY16557);

A-(SEQ ID NO: 32)-A (herein referred to as BCY16035);

A-(SEQ ID NO: 33)-A (herein referred to as BCY16043);

A-(SEQ ID NO: 34)-A-[Sar$_6$-[K-FI] (herein referred to as BCY15769);

A-(SEQ ID NO: 35)-A (herein referred to as BCY15648);

A-(SEQ ID NO: 36)-A (herein referred to as BCY16031);

A-(SEQ ID NO: 37)-A (herein referred to as BCY16079);

A-(SEQ ID NO: 38)-A (herein referred to as BCY16036);

-continued

A-(SEQ ID NO: 39)-A (herein referred to as BCY16029);

A-(SEQ ID NO: 40)-A (herein referred to as BCY16089);

A-(SEQ ID NO: 41)-A (herein referred to as BCY16088);

A-(SEQ ID NO: 42)-A (herein referred to as BCY16052);

A-(SEQ ID NO: 43)-A (herein referred to as BCY16033);

A-(SEQ ID NO: 44)-A (herein referred to as BCY16039);

Ac-(SEQ ID NO: 44) (herein referred to as BCY17988);

Ac-(SEQ ID NO: 44)-[K(N$_3$)] (herein referred to as BCY17879);

[AzPro]-(SEQ ID NO: 44) (herein referred to as BCY17880);

A-(SEQ ID NO: 45)-A (herein referred to as BCY16038);

A-(SEQ ID NO: 46)-A (herein referred to as BCY16050);

A-(SEQ ID NO: 47)-A (herein referred to as BCY16034);

A-(SEQ ID NO: 48)-A (herein referred to as BCY16032);

A-(SEQ ID NO: 49)-A (herein referred to as BCY16049);

A-(SEQ ID NO: 50)-A (herein referred to as BCY16558);

A-(SEQ ID NO: 51)-A (herein referred to as BCY16041);

A-(SEQ ID NO: 52)-A (herein referred to as BCY16042);

A-(SEQ ID NO: 53)-A (herein referred to as BCY16045);

A-(SEQ ID NO: 54)-A (herein referred to as BCY16037);

A-(SEQ ID NO: 55)-A (herein referred to as BCY16044);

A-(SEQ ID NO: 56)-A (herein referred to as BCY16040);

A-(SEQ ID NO: 57)-A-[Sar$_6$]-[K-Fl] (herein referred to as BCY15771);

A-(SEQ ID NO: 58)-A-[Sar$_6$]-[K-Fl] (herein referred to as BCY15772);

A-(SEQ ID NO: 59)-A-[Sar$_6$]-[K-Fl] (herein referred to as BCY15773);

A-(SEQ ID NO: 60)-A-[Sar$_6$]-[K-Fl] (herein referred to as BCY15774);

A-(SEQ ID NO: 61)-A-[Sar$_6$]-[K-Fl] (herein referred to as BCY15775);

A-(SEQ ID NO: 62)-A-[Sar$_6$]-[K-Fl] (herein referred to as BCY15776);

A-(SEQ ID NO: 63)-A-[Sar$_6$]-[K-Fl] (herein referred to as BCY15777);

A-(SEQ ID NO: 64)-A-[Sar$_6$]-[K-Fl] (herein referred to as BCY15770);

Ac-(SEQ ID NO: 65) (herein referred to as BCY17903);

Ac-(SEQ ID NO: 66) (herein referred to as BCY17904); and

Ac-(SEQ ID NO: 67) (herein referred to as BCY17905);

wherein AzPro represents azidopropyl, Aze represents azetidine, 1Nal represents 1-naphthylalanine, NMeTrp represents N-methyl-tryptophan, [K(N$_3$)] represents 6-azido lysine, Peg represents polyethylene glycol, Pip represents pipecolic acid, Sar represents sarcosine, Fl represents fluorescein and [K(N$_3$)(PYA-Maleimide)] represents a modified lysine having the following structure:

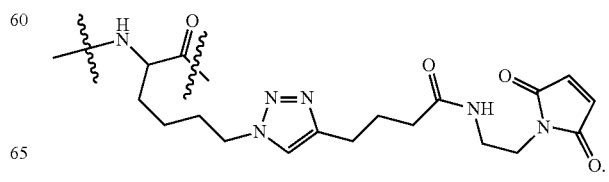

In a yet further embodiment, the molecular scaffold is TATB and the peptide ligand comprises N- and/or C-terminal additions and is selected from:

A-(SEQ ID NO: 4)-A (herein referred to as BCY13983);

A-(SEQ ID NO: 4)-A-[Sar$_6$]-[K-Fl] (herein referred to as BCY14474);

A-(SEQ ID NO: 5)-A (herein referred to as BCY13986);

A-(SEQ ID NO: 5)-A-[Sar$_6$]-[K-Fl] (herein referred to as BCY14475);

A-(SEQ ID NO: 6)-A (herein referred to as BCY15466);

A-(SEQ ID NO: 7)-A (herein referred to as BCY15467);

A-(SEQ ID NO: 8)-A (herein referred to as BCY13989);

A-(SEQ ID NO: 8)-A-[Sar$_6$]-[K-Fl] (herein referred to as BCY14476);

A-(SEQ ID NO: 9)-A (herein referred to as BCY15468);

A-(SEQ ID NO: 9)-A-[Sar$_6$]-[K-Fl] (herein referred to as BCY15768);

(SEQ ID NO: 9)-[Sar$_6$]-[K-Fl] (herein referred to as BCY15934);

Ac-(SEQ ID NO: 9)-A-[Sar$_6$-[K-Fl] (herein referred to as BCY15937);

Ac-(SEQ ID NO: 9)-[Sar$_6$]-[K-Fl] (herein referred to as BCY15938);

[Fl]G[Sar$_5$-A-(SEQ ID NO: 9)-A (herein referred to as BCY15940);

A-(SEQ ID NO: 10)-A (herein referred to as BCY15469);

A-(SEQ ID NO: 11)-A (herein referred to as BCY15470);
and

A-(SEQ ID NO: 12)-A (herein referred to as BCY15471);

wherein Sar represents sarcosine and Fl represents fluorescein.

In an alternative embodiment, the molecular scaffold is 1,1',1''-(1,3,5-triazinane-1,3,5-triyl)triprop-2-en-1-one (TATA) and the peptide ligand comprises N- and/or C-terminal additions and is:

Ac-(SEQ ID NO: 13) (herein referred to as BCY20546).

For the purpose of this description, non-inhibitory bicyclic peptides are assumed to be cyclised with TATA or TATB and yielding a tri-substituted structure. However, as will be clear from the descriptions of the invention presented herein, cyclisation may be performed with any suitable molecular scaffold which forms covalent bonds with the reactive groups of the polypeptide such that at least two polypeptide loops are formed. Cyclisation occurs on $C_i$, $C_{ii}$, and $C_{iii}$.

In a further embodiment, the pharmaceutically acceptable salt is selected from the free acid or the sodium, potassium, calcium or ammonium salt.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

Multimeric Bicyclic Peptide Ligands

According to a further aspect of the invention, there is provided a multimeric binding complex which comprises at least two bicyclic peptide ligands, wherein said peptide ligands may be the same or different, each of which comprises a peptide ligand specific for transferrin receptor 1 (TfR1) comprising a polypeptide comprising at least three reactive groups, separated by at least two loop sequences, and a molecular scaffold which forms covalent bonds with the reactive groups of the polypeptide such that at least two polypeptide loops are formed on the molecular scaffold.

Thus, in this aspect of the invention the multimeric binding complex comprises at least two (i.e. 2, 3 or 4) of any of the monomeric bicyclic peptide ligands as defined herein.

This aspect of the invention describes a series of multimerized bicyclic peptides with various chemical linkers and hinges of various lengths and rigidity using different sites of attachments within said bicyclic peptide which bind and activate TfR1 with a wide range of potency and efficacy.

It will be appreciated by the skilled person that this aspect of the invention presents multiply arranged (multimeric) bicyclic peptides which provide a synergistic benefit by virtue of the resultant properties of said multimeric binding complexes compared to the corresponding monomeric binding complexes which contain a single bicyclic peptide. For example, the multimeric binding complexes of this aspect of the invention typically have greater levels of binding potency or avidity (as measured herein by Kd values) than their monomeric counterparts. Furthermore, the multimeric binding complexes of the invention are designed to be sufficiently small enough to be cleared by the kidneys.

Without being bound by theory it is believed that multimerized bicyclic peptides are able to activate receptors by homo-crosslinking more than one of the same receptor. Thus, in one embodiment, said bicyclic peptide ligands are specific for the same target within TfR1. In a further embodiment, the multimeric binding complex comprises at least two identical bicyclic peptide ligands. By "identical" it is meant bicyclic peptides having the same amino acid sequence, most critically the same amino acid sequence refers to the binding portion of said bicyclic peptide (for example, the sequence may vary in attachment position). In this embodiment, each of the bicyclic peptides within the multimeric binding complex will bind exactly the same epitope upon the same target of TfR1—the resultant target bound complex will therefore create a homodimer (if the multimeric complex comprises two identical bicyclic peptides), homotrimer (if the multimeric complex comprises three identical bicyclic peptides) or homotetramer (if the multimeric complex comprises four identical bicyclic peptides), etc.

In an alternative embodiment, the multimeric binding complex comprises at least two differing bicyclic peptide ligands. By "differing" it is meant bicyclic peptides having a different amino acid sequence. In this embodiment, the differing bicyclic peptide ligands within the multimeric binding complex will bind to different epitopes on TfR1—the resultant target bound complex will therefore create a biparatopic (if the multimeric complex comprises two differing bicyclic peptides), triparatopic (if the multimeric complex comprises three differing bicyclic peptides) or tetraparatopic (if the multimeric complex comprises four differing bicyclic peptides), etc.

Without being bound by theory it is believed that multimerized bicyclic peptides are able to activate receptors by hetero-crosslinking differing targets, such as differing target sites on TfR1. Thus, in one embodiment, said bicyclic peptide ligands are specific for different targets on TfR1. It will be appreciated that in this embodiment, the multimeric binding complex comprises at least two differing bicyclic peptide ligands (i.e. bicyclic peptide ligands having differing amino acid sequences). In this embodiment, each of the bicyclic peptides within the multimeric binding complex will bind a differing epitope upon TfR1—the resultant target bound complex will therefore create a bispecific multimeric binding complex (if the multimeric complex comprises two differing bicyclic peptides), trispecific multimeric binding complex (if the multimeric complex comprises three differing bicyclic peptides), tetraspecific multimeric binding complex (if the multimeric complex comprises four differing bicyclic peptides), etc.

It will be appreciated that the multimeric binding complexes of the invention may be designed to be capable of binding to a range of different targets on TfR1.

The bicyclic peptides within the multimeric binding complexes of the invention may be assembled via a number of differing options. For example, there may be a central hinge or branching moiety with spacer or arm elements radiating from said hinge or branch point each of which will contain a bicyclic peptide. Alternatively, it could be envisaged that a circular support member may hold a number of inwardly or outwardly projecting bicyclic peptides.

In one embodiment, each bicyclic peptide ligand is connected to a central hinge moiety by a spacer group.

It will be appreciated that the spacer group may be linear and connect a single bicyclic peptide with the central hinge moiety. Thus, in one embodiment, the multimeric binding complex comprises a compound of formula (I):

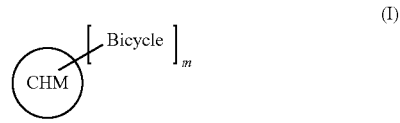

wherein CHM represents a central hinge moiety;

Bicycle represents a bicyclic peptide ligand as defined herein; and m represents an integer selected from 2 to 10.

In one embodiment, m represents an integer selected from 2, 3 or 4.

In a further embodiment, m represents 2.

When m represents 2, it will be appreciated that the central hinge moiety will require 2 points of attachment. Thus, in one embodiment, m represents 2 and CHM is a motif of formula (A):

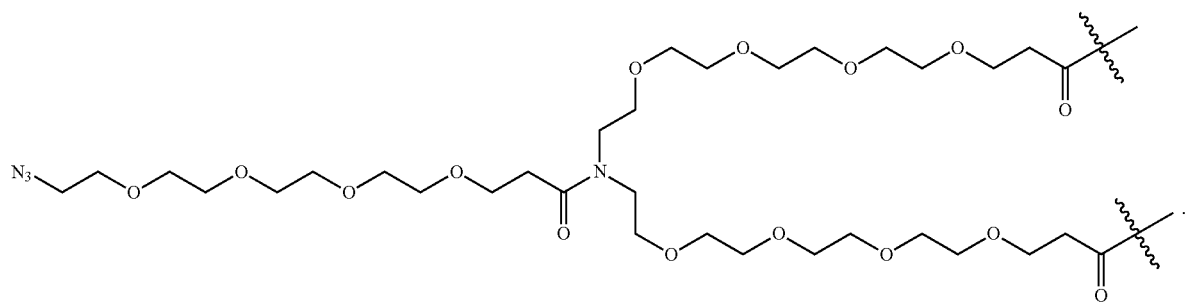

Dimers

In one embodiment, the multimeric binding complex comprises two identical bicyclic peptides and comprises a dimeric binding complex described in the following Table A:

TABLE A

Exemplified Dimeric Binding Complexes of the Invention

| Multimer Compound Number | Corresponding Monomer | Number of Monomers | Central Hinge Moiety | Attachment Point |
|---|---|---|---|---|
| BCY19409 | BCY17994 | 2 | A | C-terminus |

Numbering

When referring to amino acid residue positions within the peptides of the invention, cysteine residues ($C_i$, $C_{ii}$ and $C_{iii}$) are omitted from the numbering as they are invariant, therefore, the numbering of amino acid residues within the peptides of the invention is referred to as below:

$$-C_i-A_1-L_2-C_{ii}-N_3-D_4-W_5-T_6-L_7-P_8-W_9-H_{10}-H_{11}-C_{iii}-.$$ (SEQ ID NO: 1)

Molecular Format

N- or C-terminal extensions to the bicycle core sequence are added to the left or right side of the sequence, separated by a hyphen. For example, an N-terminal biotin-G-Sar$_5$ tail would be denoted as:

$$[Biot]-G-[Sar_5]-A-.$$ (SEQ ID NO: X)

Inversed Peptide Sequences

In light of the disclosure in Nair et al. (2003) J. Immunol. 170(3), 1362-1373, it is envisaged that the peptide sequences disclosed herein would also find utility in their retro-inverso form. For example, the sequence is reversed (i.e. N-terminus become C-terminus and vice versa) and their stereochemistry is likewise also reversed (i.e. D-amino acids become L-amino acids and vice versa).

Peptide Ligand Definition

A peptide ligand, as referred to herein, refers to a peptide, peptidic or peptidomimetic covalently bound to a molecular scaffold. Typically, such peptides, peptidics or peptidomimetics comprise a peptide having natural or non-natural amino acids, two or more reactive groups (i.e. cysteine residues) which are capable of forming covalent bonds to the scaffold, and a sequence subtended between said reactive groups which is referred to as the loop sequence, since it forms a loop when the peptide, peptidic or peptidomimetic is bound to the scaffold. In the present case, the peptides, peptidics or peptidomimetics comprise at least three cysteine residues (referred to herein as $C_i$, $C_{ii}$ and $C_{iii}$), and form at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Such advantageous properties include:

Species cross-reactivity. This is a typical requirement for preclinical pharmacodynamics and pharmacokinetic evaluation;

Protease stability. Bicyclic peptide ligands should in most circumstances demonstrate stability to plasma proteases, epithelial ("membrane-anchored") proteases, gastric and intestinal proteases, lung surface proteases, intracellular proteases and the like. Protease stability should be maintained between different species such that a bicyclic peptide lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes; and An optimal plasma half-life in the circulation. Depending upon the clinical indication and treatment regimen, it may be required to develop a bicyclic peptide with short or prolonged in vivo exposure times for the management of either chronic or acute disease states. The optimal exposure time will be governed by the requirement for sustained exposure (for maximal therapeutic efficiency) versus the requirement for short exposure times to minimise toxicological effects arising from sustained exposure to the agent.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g. —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with one or more replacement amino acids, such as an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group; modification of amino acids such as cysteine, lysine, glutamate/aspartate and tyrosine with suitable amine, thiol, carboxylic acid and phenol-reactive reagents so as to functionalise said amino acids; and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal residue is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal residue is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al. (2005) PNAS, 102(2), 413-418).

In one embodiment, the modified derivative comprises removal of any amino acid residues and substitution with alanines, such as D-alanines. This embodiment provides the advantage of identifying key binding residues and removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al., *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al., Curr. Pharmaceutical Design, (2010), 16, 3185-203, and Nestor et al., Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulphur, such as S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labelled reagent in place of the non-labelled reagent previously employed.

Molecular Scaffold

In one embodiment, the molecular scaffold comprises a non-aromatic molecular scaffold. References herein to "non-aromatic molecular scaffold" refers to any molecular scaffold as defined herein which does not contain an aromatic (i.e. unsaturated) carbocyclic or heterocyclic ring system.

Suitable examples of non-aromatic molecular scaffolds are described in Heinis et al. (2014) Angewandte Chemie, International Edition 53(6) 1602-1606.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold is 1,1',1"-(1, 3,5-triazinane-1,3,5-triyl)triprop-2-en-1-one (also known as triacryloylhexahydro-s-triazine (TATA):

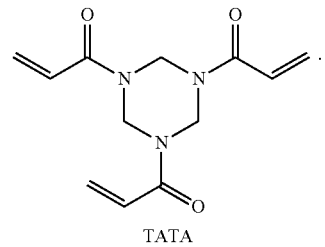

TATA

Thus, following cyclisation with the bicyclic peptides of the invention on the $C_i$, $C_{ii}$, and $C_{iii}$ cysteine residues, the molecular scaffold forms a tri-substituted 1,1',1"-(1,3,5-triazinane-1,3,5-triyl)tripropan-1-one derivative of TATA having the following structure:

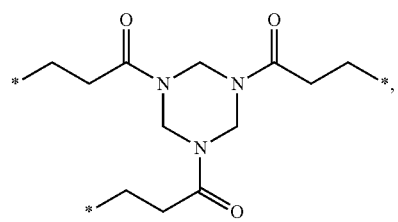

wherein * denotes the point of attachment of the three cysteine residues.

In an alternative embodiment, the molecular scaffold is 1,1',1"-(1,3,5-triazinane-1,3,5-triyl) tris(2-bromoethanone) (TATB).

Thus, following cyclisation with the bicyclic peptides of the invention on the $C_i$, $C_{ii}$, and $C_{iii}$ cysteine residues, the molecular scaffold forms a tri-substituted derivative of TATB having the following structure:

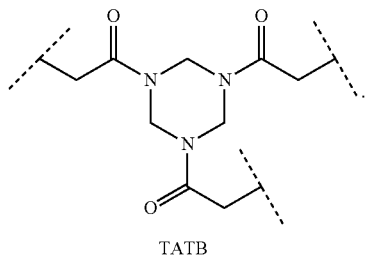

TATB

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al. (supra).

Thus, the invention also relates to the manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively, additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al. Proc Natl Acad Sci USA. 1994 Dec. 20; 91(26):12544-8 or in Hikari et al. Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA or TATB) could be added during the chemical synthesis of the first peptide so as to react with the three cysteine groups; a further cysteine or thiol could then be appended to the N- or C-terminus of the first peptide, so that this cysteine or thiol only reacted with a free cysteine or thiol of the second peptide, forming a disulphide-linked bicyclic peptide-peptide conjugate.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a peptide ligand as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Further examples of other agents which may be administered separately or in conjunction with the peptide ligands of the invention include cytokines, lymphokines, other hematopoietic factors, thrombolytic and antithrombotic factors. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered intravenously. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as transferrin receptor 1 (TfR1) binding agents. According to a further aspect of the invention, there is provided a peptide ligand or pharmaceutical composition as defined herein for use in preventing, suppressing or treating a disease or disorder through TfR1 mediated delivery of a therapeutic agent.

Transferrins are glycoproteins found in vertebrates which bind to and consequently mediate the transport of Iron (Fe) through blood plasma. It is produced in the liver and contains binding sites for two $Fe^{3+}$ atoms. Human transferrin is encoded by the TF gene and produced as a 76 kDa glycoprotein.

Transferrin glycoproteins bind iron tightly, but reversibly. Although iron bound to transferrin is less than 0.1% (4 mg) of total body iron, it forms the most vital iron pool with the highest rate of turnover (25 mg/24 h). Transferrin has a molecular weight of around 80 kDa and contains two specific high-affinity Fe(III) binding sites. The affinity of transferrin for Fe(III) is extremely high (association constant is $10^{20}$ $M^{-1}$ at pH 7.4) but decreases progressively with decreasing pH below neutrality. Transferrins are not limited to only binding to iron but also to different metal ions. These glycoproteins are located in various bodily fluids of vertebrates. When not bound to iron, transferrin is known as "apotransferrin".

In one embodiment, the transferrin is mammalian transferrin. In a further embodiment, the mammalian transferrin is human transferrin. In one embodiment, the human transferrin is human transferrin receptor 1 (TfR1; also known as CD71).

It will be appreciated that TfR1 binding peptides may be useful in the treatment of neurological disorders. Examples of such neurological disorders include but are not limited to: a neuropathy disorder, a neurodegenerative disease, cancer, an ocular disease disorder, a seizure disorder, a lysosomal storage disease, amyloidosis, a viral or microbial disease, ischemia, a behavioural disorder, and CNS inflammation.

In one embodiment, the neurological disorder is in a human subject. It will be appreciated that the dose amount and/or frequency of administration is modulated to reduce the concentration of peptide ligand to which the red blood cells are exposed. In a further embodiment, the treatment further comprises the step of monitoring the human subject for depletion of red blood cells.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Transferrin receptor 1 (TfR1) is an extensively studied model receptor-ligand system and has provided considerable insight into the cellular properties and mechanisms of nutrient/scavenger receptor cargo internalization and endocytic sorting (Qian et al (2002) Pharmacological Reviews 54(4), 561-587). TfR1 is known to undergo constitutive endocytosis and recycling to the plasma membrane and possesses pH-dependent ligand binding to enable proper sorting of endocytosed cargo. Anti-TfR1 antibodies have previously been believed to be the primary agents for TfR1 targeting of oligonucleotide therapeutics, however, the present Tfr1 binding peptide ligands of the invention have the potential for demonstrating efficient and profound knockdown of gene expression in skeletal and cardiac muscle via systemically delivered TfR1-Bicyclic Peptide-siRNA conjugates.

Thus, in light of this mechanism it is believed that the peptide ligands of the invention may find utility as tissue delivery complexes, such as delivery of the Tfr1-peptide ligand-payload (i.e. siRNA) complex to tissue cells, in particular muscle cells.

Thus, according to a further aspect of the invention there is provided a tissue delivery complex which comprises a peptide ligand of the invention bound to TfR1 in combination with a payload, such as another peptide, small molecule drug or oligonucleotide, in particular siRNA.

Said tissue delivery complexes therefore find utility in the treatment of musculoskeletal disorders. Examples of suitable musculoskeletal disorders include, but are not limited, to:

12q14 microdeletion syndrome
2q37 deletion syndrome
3M syndrome
Absence of Tibia
Absence of tibia with polydactyly
Absent patella
Acheiropody
Achondrogenesis type 1A—See Achondrogenesis
Achondrogenesis type 1B—See Achondrogenesis
Achondrogenesis type 2—See Achondrogenesis
Achondroplasia
Acro-pectoro-renal field defect
Acrocallosal syndrome, Schinzel type
Acrocapitofemoral dysplasia
Acrocephalopolydactyly
Acrodysostosis
Acrodysplasia scoliosis
Acrofacial dysostosis Catania type
Acrofacial dysostosis Palagonia type
Acrofacial dysostosis Rodriguez type
Acrofrontofacionasal dysostosis syndrome
Acromelic frontonasal dysostosis
Acromesomelic dysplasia
Acromesomelic dysplasia Hunter Thompson type Acromesomelic dysplasia Maroteaux type
Acromicric dysplasia
Acroosteolysis dominant type
Acropectoral syndrome
Acropectorovertebral dysplasia F form
Acute febrile neutrophilic dermatosis
Adactylia unilateral
Adams-Oliver syndrome
Adenosine Deaminase 2 deficiency
ADULT syndrome
Adult-onset Still's disease
Aicardi-Goutieres syndrome
Al Gazali Sabrinathan Nair syndrome
Allain-Babin-Demarquez syndrome
Alpha-mannosidosis
Amyotrophy, neurogenic scapuloperoneal, New England type
Anauxetic dysplasia
Angel shaped phalangoepiphyseal dysplasia
Ankyloblepharon-ectodermal defects-cleft lip/palate syndrome
Ankylosing spondylitis—Not a rare disease
Ankylosing vertebral hyperostosis with tylosis
Anonychia-onychodystrophy with hypoplasia or absence of distal phalanges
Antley Bixler syndrome
Apert syndrome
Arthrogryposis multiplex congenita
Arts syndrome
Aspartylglycosaminuria
Atelosteogenesis type 1
Atelosteogenesis type 2
Atelosteogenesis type 3
Auralcephalosyndactyly
Auriculo-condylar syndrome
Auriculoosteodysplasia
Autosomal dominant spondyloepiphyseal dysplasia *tarda*
Autosomal recessive early-onset inflammatory bowel disease
Autosomal recessive protein C deficiency
Axial osteomalacia
Axial spondylometaphyseal dysplasia
Baby rattle pelvic dysplasia
Baller-Gerold syndrome
Banki syndrome
Beare-Stevenson cutis gyrata syndrome
Behçet disease
Benallegue Lacete syndrome
Bethlem myopathy
Beukes familial hip dysplasia
Blau syndrome
Blount disease
BOD syndrome
Bone dysplasia Azouz type
Bone dysplasia lethal Holmgren type
Boomerang dysplasia
Bowing of legs, anterior with dwarfism
Brachycephalofrontonasal dysplasia
Brachydactylous dwarfism Mseleni type
Brachydactyly elbow wrist dysplasia
Brachydactyly long thumb type
Brachydactyly Mononen type
Brachydactyly type A1
Brachydactyly type A2
Brachydactyly type A4
Brachydactyly type A5
Brachydactyly type A6
Brachydactyly type A7
Brachydactyly type B
Brachydactyly type C
Brachydactyly type E
Brachydactyly types B and E combined
Brachyolmia type 3
Branchial arch syndrome X-linked
Brody myopathy
Bruck syndrome 1
Buschke-Ollendorff syndrome
C syndrome
Caffey disease
Campomelia Cumming type
Campomelic dysplasia
Camptobrachydactyly
Camptodactyly arthropathy coxa vara pericarditis syndrome
Camptodactyly syndrome Guadalajara type 2
Camptodactyly, tall stature, and hearing loss syndrome
Camurati-Engelmann disease
Cantu syndrome
Carpenter syndrome
Carpotarsal osteochondromatosis
Cartilage-hair hypoplasia
Catel Manzke syndrome
Cerebellar hypoplasia with endosteal sclerosis
Cerebro-costo-mandibular syndrome
Cervical dystonia
Charlie M syndrome
Cherubism
CHILD syndrome
Childhood hypophosphatasia
Chondrocalcinosis 2
Chondrodysplasia Blomstrand type
Chondrodysplasia *punctata* 1, X-linked recessive
Chondrodysplasia *punctata* Sheffield type
Chondrodysplasia with joint dislocations, GPAPP type
Chondrodysplasia, Grebe type
Chondrosarcoma
Chordoma
Chronic atypical neutrophilic dermatosis with lipodystrophy and elevated temperature
Chronic recurrent multifocal osteomyelitis
Cleft hand absent tibia
Cleidocranial dysplasia
Cleidocranial dysplasia recessive form
Cleidorhizomelic syndrome
CLOVES syndrome
Coccygodynia
CODAS syndrome
Coffin-Siris syndrome
COG1-CDG (CDG-Ilg)
Cole Carpenter syndrome
Collagenopathy type 2 alpha 1
Condensing osteitis of the clavicle
Congenital adrenal hyperplasia due to cytochrome P450 oxidoreductase deficiency
Congenital contractural arachnodactyly
Congenital femoral deficiency
Congenital primary aphakia
Congenital radioulnar synostosis
Cornelia de Lange syndrome
Cousin syndrome
Craniodiaphyseal dysplasia
Cranioectodermal dysplasia
Craniofacial dysostosis with diaphyseal hyperplasia
Craniofacial dyssynostosis Craniofrontonasal dysplasia
Craniometaphyseal dysplasia, autosomal dominant
Craniometaphyseal dysplasia, autosomal recessive type
Craniosynostosis, anal anomalies, and porokeratosis
Craniotelencephalic dysplasia
Crouzon syndrome
Culler-Jones syndrome
Currarino triad
Curry Jones syndrome
Czech dysplasia metatarsal type
Dandy-Walker malformation with postaxial polydactyly
Dandy-Walker malformation with sagittal craniosynostosis and hydrocephalus
Deficiency of interleukin-1 receptor antagonist
Delayed membranous cranial ossification
Dentatorubral-pallidoluysian atrophy
Desbuquois syndrome
Desmosterolosis
Diaphyseal medullary stenosis with malignant fibrous histiocytoma
Diastrophic dysplasia
Dihydropyrimidine dehydrogenase deficiency—Not a rare disease
Dyggve-Melchior-Clausen syndrome
Dyschondrosteosis nephritis
Dysferlinopathy
Dysosteosclerosis
Dysplasia epiphysealis hemimelica
Dyssegmental dysplasia Rolland-Desbuquois type
Dyssegmental dysplasia Silverman-Handmaker type
DYT-GNAL
EEC syndrome
EEM syndrome
Ellis-Van Creveld syndrome
Enthesitis-related juvenile idiopathic arthritis
Epidermolysa bullosa simplex with muscular dystrophy
Epiphyseal dysplasia multiple with early-onset diabetes mellitus
Erdheim-Chester disease
Ewing sarcoma
Familial avascular necrosis of the femoral head
Familial cold autoinflammatory syndrome
Familial hypocalciuric hypercalcemia type 1
Familial hypocalciuric hypercalcemia type 2
Familial hypocalciuric hypercalcemia type 3
Familial Mediterranean fever
Familial osteochondritis dissecans
Familial tumoral calcinosis
Fanconi anemia
Feingold syndrome
Felty's syndrome
Femoral facial syndrome
Femur bifid with monodactylous ectrodactyly
Femur fibula ulna syndrome
Fetal thalidomide syndrome
Fibrochondrogenesis
Fibrodysplasia ossificans progressiva
Fibular aplasia ectrodactyly
Fibular aplasia, tibial campomelia, and oligosyndactyly syndrome
Fibular hemimelia
Fibular hypoplasia and complex brachydactyly
Filippi syndrome
Fitzsimmons-Guilbert syndrome
Focal segmental glomerulosclerosis
Frank Ter Haar syndrome
Freiberg's disease
Frontofacionasal dysplasia
Frontometaphyseal dysplasia
Frontonasal dysplasia
Frontonasal dysplasia with alopecia and genital anomaly—See Frontonasal dysplasia
Frontonasal dysplasia-severe microphthalmia-severe facial clefting syndrome—See Frontonasal dysplasia
Frontorhiny—See Frontonasal dysplasia
Fryns Hofkens Fabry syndrome
Fucosidosis
Fuhrmann syndrome
Galactosialidosis
Gaucher disease type 1
Gaucher disease type 3
Geleophysic dwarfism
Genitopatellar syndrome
Genoa syndrome
Genochondromatosis
Geroderma osteodysplastica
Ghosal hematodiaphyseal dysplasia syndrome
Giant cell tumor of bone
GM1 gangliosidosis type 1
GM1 gangliosidosis type 2
GM1 gangliosidosis type 3
Goldenhar disease
Gorham's disease
*Gracile* bone dysplasia
Grant syndrome
Greenberg dysplasia
Greig cephalopolysyndactyly syndrome
Gurrieri syndrome
Hallermann-Streiff syndrome
Hand foot uterus syndrome
Hanhart syndrome
Heart-hand syndrome, Slovenian type
Heart-hand syndrome, Spanish type
Hemifacial microsomia
Hemifacial myohyperplasia
Hereditary antithrombin deficiency
Hereditary multiple osteochondromas
Holt-Oram syndrome
Hunter-McAlpine syndrome
Hurler syndrome
Hurler-Schele syndrome
Hyaline fibromatosis syndrome
Hyper-IgD syndrome
Hyperostosis corticalis generalisata
Hyperphosphatemic familial tumoral calcinosis
Hypochondroplasia
Hypophosphatasia
Hypophosphatemic rickets
I cell disease
IMAGe syndrome
Imperforate oropharynx-costo vetebral anomalies
Inclusion body myopathy 3
Inclusion body myopathy with early-onset Paget disease and frontotemporal dementia
Inclusion body myositis
Intellectual disability-spasticity-ectrodactyly syndrome
Iridogoniodysgenesis type 1
IVIC syndrome
Jackson-Weiss syndrome
Jansen type metaphyseal chondrodysplasia
Jeune syndrome
Johnson Munson syndrome
Juvenile dermatomyositis
Juvenile osteoporosis Juvenile Paget disease
Kaplan Plauchu Fitch syndrome
Kenny-Caffey syndrome type 1
Kenny-Caffey syndrome type 2
Keutel syndrome
Kienbock's disease
Kleiner Holmes syndrome
Klippel Feil syndrome
Klippel-Trenaunay syndrome
Kniest dysplasia
Kniest like dysplasia lethal
Kohler disease
Kyphomelic dysplasia
Lacrimo-auriculo-dento-digital syndrome
Lambdoid synostosis
Lambert Eaton myasthenic syndrome
Langer mesomelic dysplasia
Larsen syndrome
Lateral meningocele syndrome
Laurin-Sandrow syndrome
Legg-Calve-Perthes disease
Lenz Majewski hyperostotic dwarfism
Leri pleonosteosis
Leri Weill dyschondrosteosis
Lethal chondrodysplasia Moerman type
Lethal chondrodysplasia Seller type
Levator syndrome
Limb-girdle muscular dystrophy type 1A
Limb-girdle muscular dystrophy type 2A
Limb-girdle muscular dystrophy type 2B
Limb-girdle muscular dystrophy type 2E
Limb-girdle muscular dystrophy type 2F
Limb-girdle muscular dystrophy type 2H
Limb-girdle muscular dystrophy, type 2C
Limb-girdle muscular dystrophy, type 2D
Limb-mammary syndrome
Loeys-Dietz syndrome
Lowry Maclean syndrome
Lowry Wood syndrome
Macrophagic myofasciitis
Maffucci syndrome
MAGIC syndrome
Majeed syndrome
Mandibuloacral dysplasia with type A lipodystrophy
Mandibuloacral dysplasia with type B lipodystrophy
Mandibulofacial dysostosis with microcephaly
Mannosidosis, beta A, lysosomal
Marshall syndrome
Marshall-Smith syndrome
McCune-Albright syndrome
Meckel syndrome
Median cleft of upper lip with polyps of facial skin and nasal mucosa
Meier-Gorlin syndrome
Melnick-Needles syndrome
Melorheostosis
Melorheostosis with osteopoikilosis
Mesomelia-synostoses syndrome
Mesomelic dwarfism cleft palate camptodactyly
Mesomelic dysplasia Kantaputra type
Mesomelic dysplasia Savarirayan type
Metacarpals 4 and 5 fusion
Metachondromatosis
Metaphyseal acroscyphodysplasia
Metaphyseal chondrodysplasia Schmid type
Metaphyseal chondrodysplasia Spahr type
Metaphyseal dysostosis-intellectual disability-conductive deafness syndrome
Metaphyseal dysplasia maxillary hypoplasia brachydactyly
Metaphyseal dysplasia without hypotrichosis
Metatropic dysplasia
Mevalonic aciduria
Microcephalic osteodysplastic primordial dwarfism type 1
Microcephalic osteodysplastic primordial dwarfism type 2
Microcephalic primordial dwarfism Toriello type
Microsomia hemifacial radial defects
Miller syndrome
Minicore myopathy with external ophthalmoplegia
Monomelic amyotrophy
Muckle-Wells syndrome
Mucolipidosis III alpha/beta
Mucolipidosis type 4
Mucopolysaccharidosis type III
Mucopolysaccharidosis type IIIA
Mucopolysaccharidosis type IIIB
Mucopolysaccharidosis type IIIC
Mucopolysaccharidosis type IIID
Mucopolysaccharidosis type IV
Mucopolysaccharidosis type IVA
Mucopolysaccharidosis type VII
Muenke Syndrome
Multicentric carpotarsal osteolysis syndrome
Multiple epiphyseal dysplasia
Multiple epiphyseal dysplasia 2
Multiple sulfatase deficiency
Multiple synostoses syndrome 1
Multiple system atrophy
Muscular dystrophy
Muscular dystrophy, congenital, megaconial type
MYH7-related scapuloperoneal myopathy
Myhre syndrome
Myosinopathies
Myostatin-related muscle hypertrophy
Myotonic dystrophy
Myotonic dystrophy type 2
Nager acrofacial dysostosis
Nail-patella syndrome
Nakajo Nishimura syndrome
Neonatal Onset Multisystem Inflammatory disease
Neonatal severe hyperparathyroidism
Nestor-guillermo progeria syndrome
Neurofibromatosis type 1
Nievergelt syndrome
Normophosphatemic familial tumoral calcinosis
Occipital horn syndrome
Oculoauriculofrontonasal syndrome
Oculodentodigital dysplasia
Oculomaxillofacial dysostosis
Oculopharyngeal muscular dystrophy
Oliver syndrome
Ollier disease
Omodysplasia 1
Omodysplasia 2
Opsismodysplasia
Orofaciodigital syndrome 1
Orofaciodigital syndrome 10
Orofaciodigital syndrome 11
Orofaciodigital syndrome 2
Orofaciodigital syndrome 3
Orofaciodigital syndrome 4

Orofaciodigital syndrome 5
Orofaciodigital syndrome 6
Orofaciodigital syndrome 8
Orofaciodigital syndrome 9
Oslam syndrome
OSMED Syndrome
Ossification of the posterior longitudinal ligament of the spine—Not a rare disease
Osteoarthropathy of fingers familial
Osteochondritis dissecans
Osteodysplasia familial Anderson type
Osteodysplasty precocious of Danks Mayne and Kozlowski
Osteofibrous dysplasia
Osteogenesis imperfecta type 1
Osteogenesis imperfecta type II
Osteogenesis imperfecta type III
Osteogenesis imperfecta type IV
Osteogenesis imperfecta type V
Osteogenesis imperfecta type VI
Osteoglophonic dysplasia
Osteomesopyknosis
Osteopathia striata with cranial sclerosis
Osteopenia and sparse hair
Osteopetrosis autosomal dominant type 1
Osteopetrosis autosomal dominant type 2
Osteopetrosis autosomal recessive 3
Osteopetrosis autosomal recessive 4
Osteopetrosis autosomal recessive 7
Osteopoikilosis and dacryocystitis
Osteoporosis oculocutaneous hypopigmentation syndrome
Osteoporosis-pseudoglioma syndrome
Osteosarcoma
Oto-palato-digital syndrome type 1
Oto-palato-digital syndrome type 2
Pachydermoperiostosis
Pacman dysplasia
Pallister-Hall syndrome
Paramyotonia congenita
Parastremmatic dwarfism
PARC syndrome
Parkes Weber syndrome
Patterson-Stevenson-Fontaine syndrome
Pelvic dysplasia arthrogryposis of lower limbs
Periodic fever, aphthous stomatitis, pharyngitis and adenitis
Pfeiffer-type cardiocranial syndrome
Phocomelia ectrodactyly deafness sinus arrhythmia
Pigmented villonodular synovitis
Piriformis syndrome
Platyspondylic lethal skeletal dysplasia Torrance type
Pleoconial myopathy with salt craving
Poland syndrome
Polycystic bone disease
Polycystic lipomembranous osteodysplasia with sclerosing leukoencephalopathy
Polydactyly myopia syndrome
Polyostotic osteolytic dysplasia, hereditary expansile
Potassium aggravated myotonia
Preaxial deficiency, postaxial polydactyly and hypospadias
Preaxial polydactyly type 1
Preaxial polydactyly type 2
Preaxial polydactyly type 3
Preaxial polydactyly type 4
Progeria
Progressive osseous heteroplasia
Progressive pseudorheumatoid dysplasia
Protein C deficiency—Not a rare disease
Proteus syndrome
Proximal symphalangism
Pseudoachondroplasia
Pseudoaminopterin syndrome
Pseudodiastrophic dysplasia
Pseudohypoparathyroidism type 1A
Pseudohypoparathyroidism type 1C
Pseudopseudohypoparathyroidism
Psoriatic juvenile idiopathic arthritis
Pycnodysostosis
Pyknoachondrogenesis
Pyle disease
Pyoderma gangrenosum
Pyogenic arthritis, pyoderma gangrenosum and acne
Radio-ulnar synostosis type 1—See Congenital radioulnar synostosis
Radio-ulnar synostosis type 2—See Congenital radioulnar synostosis
Radioulnar synostosis-microcephaly-scoliosis syndrome
Raine syndrome
Ramon Syndrome
Rapadilino syndrome
Reactive arthritis
Renal dysplasia, retinal pigmentary dystrophy, cerebellar ataxia and skeletal dysplasia
Retinal vasculopathy with cerebral leukodystrophy with systemic manifestations
Rhizomelic chondrodysplasia punctata type 1
Rhizomelic dysplasia Patterson Lowry type
Rhizomelic syndrome
Richieri Costa Da Silva syndrome
Rigid spine syndrome
Roberts syndrome
Saethre-Chotzen syndrome
Salla disease—See Free sialic acid storage disease
SAPHO syndrome
Sarcoidosis—Not a rare disease
Say Meyer syndrome
Say-Field-Coldwell syndrome
Scalp defects postaxial polydactyly
SCARF syndrome
Scheie syndrome
Scheuermann disease
Schimke immunoosseous dysplasia
Schinzel Giedion syndrome
Schinzel type phocomelia
Schneckenbecken dysplasia
Schnitzler syndrome
Schwartz Jampel syndrome
Sclerosteosis
Seckel syndrome
Sepiapterin reductase deficiency
Short rib-polydactyly syndrome type 3
Short rib-polydactyly syndrome type 1
Short rib-polydactyly syndrome type 4
Short rib-polydactyly syndrome, Majewski type
Short stature syndrome, Brussels type
Shprintzen-Goldberg craniosynostosis syndrome
Shwachman-Diamond syndrome
Sickle beta thalassemia
Sickle cell anemia
Sillence syndrome
Singleton-Merten syndrome
Slipped capital femoral epiphysis—Not a rare disease Small patella syndrome
Smith McCort dysplasia
Smith-Lemli-Opitz syndrome
Sotos syndrome
Spheroid body myopathy
Spinal muscular atrophy Ryukyuan type
Spinal muscular atrophy type 1 with congenital bone fractures
Spinal muscular atrophy type 3
Spinal muscular atrophy type 4
Spinal muscular atrophy with respiratory distress 1
Splenogonadal fusion limb defects micrognatia
Split hand foot malformation
Split hand split foot nystagmus
Spondylocamptodactyly
Spondylocarpotarsal synostosis syndrome
Spondylocostal dysostosis 1—See Spondylocostal dysostosis
Spondylocostal dysostosis 2—See Spondylocostal dysostosis
Spondylocostal dysostosis 3—See Spondylocostal dysostosis
Spondylocostal dysostosis 4—See Spondylocostal dysostosis
Spondylocostal dysostosis 5—See Spondylocostal dysostosis
Spondylocostal dysostosis 6—See Spondylocostal dysostosis
Spondylodysplastic Ehlers-Danlos syndrome
Spondyloenchondrodysplasia with immune dysregulation
Spondyloepimetaphyseal dysplasia Genevieve type
Spondyloepimetaphyseal dysplasia joint laxity
Spondyloepimetaphyseal dysplasia Matrilin-3 related
Spondyloepimetaphyseal dysplasia Missouri type
Spondyloepimetaphyseal dysplasia Shohat type
Spondyloepimetaphyseal dysplasia Sponastrime type
Spondyloepimetaphyseal dysplasia Strudwick type
Spondyloepimetaphyseal dysplasia with hypotrichosis
Spondyloepimetaphyseal dysplasia with multiple dislocations
Spondyloepimetaphyseal dysplasia X-linked
Spondyloepimetaphyseal dysplasia, Aggrecan type
Spondyloepiphyseal dysplasia congenita
Spondyloepiphyseal dysplasia Maroteaux type
Spondyloepiphyseal dysplasia *tarda* X-linked
Spondyloepiphyseal dysplasia-brachydactyly and distinctive speech
Spondylometaepiphyseal dysplasia short limb-hand type
Spondylometaphyseal dysplasia Algerian type
Spondylometaphyseal dysplasia corner fracture type
Spondylometaphyseal dysplasia Sedaghatian type
Spondylometaphyseal dysplasia type A4
Spondylometaphyseal dysplasia with cone-rod dystrophy
Spondylometaphyseal dysplasia with dentinogenesis imperfecta
Spondylometaphyseal dysplasia X-linked
Spondylometaphyseal dysplasia, Kozlowski type
Spondyloperipheral dysplasia
Spondylothoracic dysostosis
Sprengel deformity
STAR syndrome
Stiff person syndrome
Stuve-Wiedemann syndrome
Symphalangism with multiple anomalies of hands and feet
Syndactyly Cenani Lenz type
Syndactyly type 3
Syndactyly type 5
Syndactyly type 9
Syndactyly-polydactyly-earlobe syndrome
Syngnathia multiple anomalies
Synovial Chondromatosis
Systemic onset juvenile idiopathic arthritis
TAR syndrome
TARP syndrome
Tarsal carpal coalition syndrome
Tarsal tunnel syndrome
Tetra-amelia syndrome
Tetraamelia-multiple malformations syndrome
Tetramelic monodactyly
Thanatophoric dysplasia type 1
Thanatophoric dysplasia type 2
Thoracic dysplasia hydrocephalus syndrome
Thoracolaryngopelvic dysplasia
Tibia absent polydactyly arachnoid cyst
Tietze syndrome
TMEM165-CDG (CDG-IIk)
Townes-Brocks syndrome
Treacher Collins syndrome
Tricho-dento-osseous syndrome
Trichohepatoenteric syndrome
Trichorhinophalangeal syndrome type 1
Trichorhinophalangeal syndrome type 2
Trichorhinophalangeal syndrome type 3
Trigonobrachycephaly, bulbous bifid nose, micrognathia, and abnormalities of the hands and feet
Triphalangeal thumbs brachyectrodactyly
Trochlea of the humerus aplasia of
Trochlear dysplasia
Troyer syndrome
Tubular aggregate myopathy
Tumor necrosis factor receptor-associated periodic syndrome
Ulna and fibula, hypoplasia of
Ulna hypoplasia-intellectual disability syndrome
Ulna metaphyseal dysplasia syndrome
Ulnar hypoplasia lobster claw deformity of feet
Ulnar-mammary syndrome
Undifferentiated pleomorphic sarcoma
Upington disease
Verloes Bourguignon syndrome
Viljoen Kallis Voges syndrome
Warman Mulliken Hayward syndrome
Weaver syndrome
Weill-Marchesani syndrome
Weissenbacher-Zweymuller syndrome
Weyers acrofacial dysostosis
Wildervanck syndrome
Worth type autosomal dominant osteosclerosis
Wrinkly skin syndrome
X-linked dominant chondrodysplasia *punctata* 2
X-linked dominant scapuloperoneal myopathy
X-linked hypophosphatemia
X-linked intellectual disability-plagiocephaly syndrome
X-linked skeletal dysplasia-intellectual disability syndrome
Yunis-Varon syndrome The invention is further described below with reference to the following examples.

EXAMPLES

Materials and Methods
Preparation of Bicyclic Peptide Ligands (General Method)

Bicycle peptides were synthesized on Rink amide resin using standard Fmoc (9-fluorenylmethyloxycarbonyl) solid-phase peptide synthesis, either by manual coupling (for large scale) or using a Biotage Syroll automated peptide synthesizer (for small scale). Following TFA-based cleavage from the resin, peptides were precipitated with diethyl ether and dissolved in 50:50 acetonitrile/water. The crude peptides (at ~1 mM concentration) were then cyclized with 1.3 equiv. of the scaffold, using ammonium bicarbonate (100 mM) as a base. Completion of cyclization was determined by matrix-assisted laser desorption ionization time-of-flight (MALDI-TOF) or LC-MS. Once complete, the cyclization reaction was quenched using N-acetyl cysteine (10 equiv. with respect to the peptide), and the solutions were lyophilized. The residue was dissolved in an appropriate solvent and purified by RP-HPLC. Peptide fractions of sufficient purity and the correct molecular weight (verified by either MALDI-TOF and HPLC or LC-MS) were pooled and lyophilized. Concentrations were determined by UV absorption using the extinction coefficient at 280 nm, which was based on Trp/Tyr content.

All amino acids, unless noted otherwise, were used in the L-configurations.

Biological Data

1. TfR1 Direct Binding Assay

Affinity of the peptides of the invention for human or cynomolgus TfR1 (Kd) was determined using a fluorescence polarisation assay, in accordance with the following method. Peptides of the invention were labelled with a fluorescent tag (fluorescein) and diluted to 2.5 nM in 25 mM HEPES with 100 mM NaCl, 4 mM $CaCl_2$ and 0.005% P20, pH 7.4. TfR1 protein (Human: R&D Systems, 2474-TR or Acro Biosystems, CD1-H5243; Cyno: Acro Biosystems, TFR-C524a) was titrated starting at 1-5 μM in the same assay buffer as the peptide to assay 1 nM peptide in a total volume of 25 μL in black walled and bottomed low bind low volume 384 well plates. The assay was typically set up by adding 5 μL assay buffer, 10 μL TfR1 protein then 10 μL fluorescent peptide. The concentrations of TfR1 protein were 1 in 2 serial dilutions to give 12 different concentrations starting at 1-5 μM. Measurements were conducted on a BMG PHERAstar FS equipped with an FP 485 520 520 optic module at 25° C. with 200 flashes per well and a positioning delay of 0.1 second. Each well was measured every 5 minutes for 60 minutes. The gain used for analysis was determined for each tracer at the end of the 60 minutes where there was no protein in the well. The mP were fit to a standard 1:1 binding model with a quadratic equation to generate a Kd value. Selected peptides of the invention were tested in the above mentioned assay and the results are shown in Table 1:

TABLE 1

FP Direct Binding of Selected Peptide Ligands of the Invention

| Peptide Ligand | Geomean Kd (μM) Human TfR1 | Standard Deviation (SD) | Geomean Kd (μM) Cyno TfR1 | Standard Deviation (SD) |
|---|---|---|---|---|
| BCY12652 | 0.298 | 0.215 (n = 9) | 0.098 | 0.035 (n = 3) |
| BCY12650 | 0.862 | 0.118 (n = 3) | nd | nd |
| BCY12651 | 0.971 | 0.633 (n = 5) | nd | nd |

TABLE 1-continued

FP Direct Binding of Selected Peptide Ligands of the Invention

| Peptide Ligand | Geomean Kd (μM) Human TfR1 | Standard Deviation (SD) | Geomean Kd (μM) Cyno TfR1 | Standard Deviation (SD) |
|---|---|---|---|---|
| BCY14474 | 0.751 | 2.1419 (n = 2) | nd | nd |
| BCY14475 | 0.078 | 0.0664 (n = 2) | 2.617 | 0 (n = 1) |
| BCY14476 | 0.087 | 0.0327 (n = 8) | 3.6549 | 0 (n = 1) |
| BCY15768 | 0.047 | 0.0171 (n = 6) | 0.70684 | 0 (n = 1) |
| BCY15934 | 0.064 | 0.0067 (n = 2) | nd | nd |
| BCY15937 | 0.034 | 0.0000 (n = 1) | nd | nd |
| BCY15938 | 0.060 | 0.0014 (n = 2) | nd | nd |
| BCY15940 | 0.054 | 0.0002 (n = 2) | nd | nd | nd = not determined

2. TfR1 SPR Binding Assay

Biacore experiments were performed to determine $k_a$ ($M^{-1} s^{-1}$), $k_d$ ($s^{-1}$), $K_D$ (nM) values of various peptides binding to TfR1.

Recombinant human and cynomolgus TfR1 were received from Bicycle as $His_6$-tagged TfR1 (a.a. 89-760) (ACRO Biosystems, CD1-H5243 and TFR-C524a).

For analysis of TfR1 peptide binding, a Biacore T200 or S200 instrument was used utilising a capture/coupling approach with a Cytiva NTA chip at 25° C. with 25 mM HEPES, 0.1M NaCl, 0.05% Tween 20 pH 7.4 as the running buffer. Immobilisation was carried out as follows. The chip was pre-equilibrated with an injection of 500 mM EDTA (pH 8), before activation with 5 mM $NiSO_4$. The surface was then activated using standard amine-coupling chemistry. Briefly, the carboxymethyl dextran surface was activated with a 1:1 ratio of 0.4 M 1-ethyl-3-(3-dimethylaminopropyl) carbodiimide hydrochloride (EDC)/0.1 M N-hydroxy succinimide (NHS). The TfR1 protein (human or cynomolgus) was then captured onto the activated surface after dilution into running buffer to 200 nM and 250 nM respectively. Residual activated groups were blocked with a 7 min injection of 1 M ethanolamine (pH 8.5):HBS-N (1:1). Reference surfaces were activated and blocked as above with no TfR1 protein capture. Capture levels were in the range of 1,500-5,000 RU dependent upon the individual study Buffer was changed to 25 mM HEPES, 0.1M NaCl, 0.05% Tween 20 pH 7.4 1% DMSO.

A dilution series of test peptides was prepared in this buffer with a top peptide concentration of 5 μM and 6 further 2-fold dilutions. The SPR analysis was run at 25° C. at a flow rate of 30 μl/min with 160 seconds association and 700-800 seconds dissociation. Data were corrected for DMSO excluded volume effects. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Selected peptides of the invention were tested in the above mentioned assay and the results are shown in Table 2:

TABLE 2

SPR Binding of Selected Peptide Ligands of the Invention

| Peptide Ligand | Geomean Kd (μM) Human TfR1 | Standard Deviation (SD) | Geomean Kd (μM) Cyno TfR1 | Standard Deviation (SD) |
|---|---|---|---|---|
| BCY12455 | 65.600 | 72.8 | 42.384 | 34.0 |
| BCY13983 | 450.0 | 0 (n = 1) | 4580 | 0 (n = 1) |

TABLE 2-continued

SPR Binding of Selected Peptide Ligands of the Invention

| Peptide Ligand | Geomean Kd (μM) Human TfR1 | Standard Deviation (SD) | Geomean Kd (μM) Cyno TfR1 | Standard Deviation (SD) |
|---|---|---|---|---|
| BCY13986 | 132.0 | 148 (n = 4) | 2590 | 0 (n = 1) |
| BCY15466 | 32.1 | 6.7 (n = 4) | 1394.3 | 465.6 (n = 4) |
| BCY15467 | 29.5 | 29.5 (n = 5) | 1580.8 | 516.6 (n = 3) |
| BCY13989 | 376.3 | 44.5 (n = 4) | 3440.5 | 2347.6 (n = 2) |
| BCY15468 | 37.8 | 28.4 (n = 5) | 1717.6 | 2143.6 (n = 4) |
| BCY15469 | 54.3 | 29.9 (n = 4) | 2117.7 | 1347.0 (n = 4) |
| BCY15470 | 36.4 | 16.1 (n = 4) | 1615.1 | 1036.7 (n = 4) |
| BCY15471 | 262.9 | 109.8 (n = 5) | 4660 | 0 (n = 1) |

Further selected peptides of the invention were tested in the above mentioned assay and the results are shown in Table 3:

TABLE 3

SPR Binding of Selected Peptide Ligands of the Invention

| Peptide Ligand | Human TfR1 Kd (nM) | Cynomolgus TfR1 Kd (nM) |
|---|---|---|
| BCY13989 | nd | ~11000 |
| BCY 15768 | nd | 3800 |
| BCY 15769 | 70 | 2200 |
| BCY 15771 | 65 | 4000 |
| BCY 15772 | nd | 99000 |
| BCY 15773 | 178 | 2600 |
| BCY 15774 | nd | 41000 |
| BCY 15775 | nd | NB |
| BCY 15776 | nd | NB |
| BCY 15777 | nd | NB |
| BCY 15770 | nd | >100000 |
| BCY 15891 | 46 | 3990 |
| BCY 17992 | 42 | 535 |
| BCY 17993 | 9 | 235 |
| BCY 18033 | nd | 589 |
| BCY 18034 | 25 | 2080 |
| BCY 18035 | 77 | 10300 |
| BCY 18036 | 422 | 7310 |
| BCY 17994 | 6.6, 22 | 688 |
| BCY 17995 | 3.4 | nd |
| BCY 18037 | 11 | 1080 |
| BCY 18038 | 9.7 | 1650 |
| BCY 18039 | 8.6 | 819 |
| BCY 17109 | 3.2 | 281*/535 |
| BCY 17114 | 48 | 845 |
| BCY 17110 | 15 | 232 |
| BCY 17111 | 8.3 | 907 |
| BCY 17112 | 4.6 | 2604 |
| BCY 17113 | 308 | 1664 |
| BCY 17115 | 60 | 1242 |
| BCY 17116 | 1 | 474 |
| BCY 17117 | 4.2 | 805 |
| BCY 17118 | 120 | 1959 |
| BCY 17119 | 212 | 5653 |
| BCY 17120 | 32 | 1257 |
| BCY 15468 | 29 | 4015 |
| BCY 16048 | 28 | 1280 |
| BCY 16049 | 175 | 28000 |
| BCY 16035 | 37 | 4600 |
| BCY 16047 | 49 | 4828 |
| BCY 16039 | 89 | 10234 |
| BCY 16036 | 83 | 5902 |
| BCY 16033 | 82 | 6664 |
| BCY 16038 | 210 | ~10000 |
| BCY 16050 | 210 | 25800 |
| BCY 16053 | 33 | 3120 |
| BCY 16089 | 63 | 7466 |
| BCY 16088 | 67 | 5878 |
| BCY 16034 | 238 | 25000 |
| BCY 16045 | nd | 10000 |
| BCY 16046 | 32 | 2089 |
| BCY 16051 | 25 | 1820 |
| BCY 16031 | 68 | 6481 |
| BCY 16079 | 60 | 5665 |
| BCY 16029 | 47 | 5483 |
| BCY 16052 | 73 | 7478 |
| BCY 16032 | 305 | 30000 |
| BCY 16550 | 18 | 682 |
| BCY 16753 | 12 | 1700 |
| BCY 16962 | 6.1 | 599 |
| BCY 16963 | nd | 501 |
| BCY 16964 | 6.6 | 514 |
| BCY 16966 | 11 | 1900 |
| BCY 16557 | 20 | 1180 |
| BCY 16558 | 20000 | 50000 |
| BCY 17986 | 52 | 4660 |
| BCY 17987 | 50 | 5140 |
| BCY 17988 | 649 | nd |
| BCY 17991 | 3.4 | 35 |
| BCY 20546 | 1660 | nd |
| BCY 17986 | 52 | 4660 |
| BCY 17988 | 649 | nd |
| BCY 17994 | 6.6, 22 | 688 | nd = not determined
NB = no binding

3. TfR1 Inhibition Assay

TfR1 inhibitory activity of peptides of the invention (IC$_{50}$) was determined using Alpha assay, in accordance with the following method. Proteins, peptides and Alpha reagents were prepared to 5× concentration and 5 μl of each reagent added to 25 μl total volume in white 384-well Optiplate to make 1× final concentration. Fluorescently labelled human transferrin (Invitrogen, T2871) was diluted to 2.5 nM in 25 mM HEPES with 100 mM NaCl, 4 mM CaCl$_2$, 0.5% BSA and 0.05% P20, pH 7.4. Human or cynomolgus TfR1 protein was diluted to 50 nM and unlabelled human transferrin (R&D Systems, 2914-HT) was diluted to 500 nM in the same assay buffer. Non-labelled peptides from DMSO stock were diluted 20-fold in the same assay buffer, followed by 1 in 3 serial dilution in assay buffer containing 5% DMSO to give 11-different concentrations. 5 μl fluorescently labelled transferrin, 5 μl human or cynomolgus TfR1, 5 μl non-labelled peptide or unlabelled human transferrin (R&D Systems, 2914-HT) were added to white 384-well Optiplate and incubated for 30 min. Anti-FITC Acceptor (PerkinElmer, AL127) was diluted 50-fold in assay buffer, 5 μl added to assay plate and incubated for 30 min. Nickel Chelate Donor (PerkinElmer, AS101) was diluted 50-fold in assay buffer, 5 μl added to assay plate and incubated for 180 min. Luminescence measurements were conducted on a BMG PHERAstar FS or FSX equipped with an AlphaScreen 520-620 module at 25° C. following excitation at 680 nm. Raw data was normalized to 100 nM unlabelled transferrin and buffer. Data was standardized to 100 nM unlabelled transferrin and buffer controls and fit to standard 4 parameter fit to generate IC50 value.

Selected peptides of the invention were tested in the above mentioned assay and the results are shown in Table 4:

TABLE 4

Transferrin Inhibition Assay for Selected Peptide Ligands of the Invention

| Peptide Ligand | Geomean IC50 (μM) Human TfR1 | Standard Deviation (SD) | Geomean IC50 (μM) Cyno TfR1 | Standard Deviation (SD) |
|---|---|---|---|---|
| BCY12455 | 0.673 | 0.147 (n = 4) | nd | nd |
| BCY12452 | 1.215 | 0.564 (n = 2) | nd | nd |
| BCY12454 | 0.893 | 0.356 (n = 2) | nd | nd | nd = not determined

4. TfR1 Competition Binding Assay

Peptides without a fluorescent tag were tested in competition with 1 nM of a peptide with a fluorescent tag and a known Kd (BCY15768). Peptides were first diluted 100% DMSO then diluted to an appropriate concentration in assay buffer as described in the direct binding assay with a maximum of 2.5% DMSO, then serially diluted 1 in 2. Ten μL of diluted peptide was added to the plate followed by 10 μL of human TfR1 as described in direct binding assay at a fixed concentration (200 nM). Then 5 μL fluorescent peptide added. Measurements were conducted as for the direct binding assay, however the gain was determined prior to the first measurement. Data analysis was in Dotmatics where equation was fit to Cheng-Prusoff.

Selected peptides of the invention were tested in the above mentioned assay and the results are shown in Table 5:

TABLE 5

TfR1 Competition Binding Assay for Selected Peptide Ligands of the Invention

| Peptide Ligand | Geomean Ki (μM) | Standard Deviation (SD) |
|---|---|---|
| BCY17991 | 0.002 | 0.001 |
| BCY17995 | 0.002 | 0.003 |
| BCY17993 | 0.003 | 0.002 |
| BCY18033 | 0.004 | 0.002 |
| BCY18030 | 0.005 | 0.003 |
| BCY18039 | 0.008 | n = 1 |
| BCY17994 | 0.008 | 0.010 |
| BCY18029 | 0.008 | 0.004 |
| BCY17109 | 0.009 | 0.006 |
| BCY18037 | 0.011 | 0.000 |
| BCY17990 | 0.011 | 0.010 |
| BCY17992 | 0.012 | 0.007 |
| BCY18038 | 0.012 | 0.001 |
| BCY18034 | 0.014 | 0.006 |
| BCY18031 | 0.020 | 0.006 |
| BCY18035 | 0.020 | 0.005 |
| BCY17110 | 0.022 | 0.005 |
| BCY17115 | 0.030 | 0.012 |
| BCY17989 | 0.030 | 0.019 |
| BCY16962 | 0.036 | 0.025 |
| BCY17117 | 0.037 | 0.003 |
| BCY16963 | 0.039 | 0.030 |
| BCY15889 | 0.040 | 0.005 |
| BCY17114 | 0.041 | 0.012 |
| BCY17987 | 0.042 | 0.015 |
| BCY15893 | 0.044 | 0.006 |
| BCY16754 | 0.044 | 0.024 |
| BCY17112 | 0.047 | n = 1 |
| BCY15890 | 0.047 | 0.014 |
| BCY16753 | 0.048 | 0.021 |
| BCY16046 | 0.049 | 0.008 |
| BCY15466 | 0.050 | 0.013 |
| BCY17120 | 0.052 | 0.002 |
| BCY16964 | 0.052 | 0.008 |
| BCY16965 | 0.052 | 0.018 |
| BCY17986 | 0.054 | 0.021 |
| BCY15470 | 0.055 | 0.007 |
| BCY16550 | 0.056 | 0.029 |
| BCY16966 | 0.063 | 0.017 |
| BCY15892 | 0.063 | 0.005 |
| BCY16051 | 0.066 | 0.018 |
| BCY15891 | 0.067 | 0.027 |
| BCY17118 | 0.070 | 0.017 |
| BCY16048 | 0.071 | 0.016 |
| BCY17116 | 0.075 | 0.016 |
| BCY16053 | 0.075 | 0.021 |
| BCY16557 | 0.078 | 0.058 |
| BCY17111 | 0.086 | 0.010 |
| BCY18036 | 0.090 | 0.012 |
| BCY16035 | 0.091 | 0.007 |
| BCY17113 | 0.103 | 0.028 |
| BCY18032 | 0.105 | 0.046 |
| BCY15648 | 0.107 | 0.028 |
| BCY15469 | 0.119 | 0.032 |
| BCY16031 | 0.119 | 0.014 |
| BCY16079 | 0.123 | 0.012 |
| BCY15939 | 0.125 | 0.028 |
| BCY16036 | 0.127 | 0.031 |
| BCY16029 | 0.131 | 0.009 |
| BCY16047 | 0.133 | 0.039 |
| BCY15467 | 0.133 | 0.036 |
| BCY16089 | 0.136 | 0.018 |
| BCY17119 | 0.160 | 0.012 |
| BCY16088 | 0.161 | 0.026 |
| BCY16052 | 0.169 | 0.034 |
| BCY16033 | 0.180 | 0.010 |
| BCY16039 | 0.219 | 0.021 |
| BCY16038 | 0.221 | 0.030 |
| BCY17988 | 0.272 | 0.099 |
| BCY15935 | 0.300 | 0.333 |
| BCY15894 | 0.392 | 0.202 |
| BCY15471 | 0.434 | 0.124 |
| BCY16050 | 0.473 | 0.091 |
| BCY16034 | 0.510 | 0.202 |
| BCY13989 | 0.565 | 0.550 |
| BCY16032 | 0.654 | 0.042 |
| BCY16049 | 0.805 | 0.728 |
| BCY16558 | 1.623 | n = 1 |
| BCY16041 | 2.189 | 0.629 |
| BCY16042 | 3.451 | 0.783 |
| BCY16045 | 6.866 | 7.594 |
| BCY16037 | 9.220 | 8.922 |
| BCY16044 | 13.900 | 0.000 |
| BCY16040 | 20.000 | 0.000 |
| BCY16043 | 23.600 | 0.000 |

Selected peptides of the invention were tested in the above mentioned assay using human and/or cynomolgus TfR1 and the results are shown in Table 6:

TABLE 6

TfR1 Competition Binding Assay for Selected Peptide Ligands of the Invention

| Peptide Ligand | Human TfR1 Ki (nM) | Cynomolgus TfR1 Ki (nM) |
|---|---|---|
| BCY 13989 | 565 | 3440 |
| BCY 14476 | 79 | nd |
| BCY 15469 | 119 | 2117 |
| BCY 15892 | 63 | nd |
| BCY 15470 | 55 | 1615 |
| BCY 15893 | 44 | nd |
| BCY 15471 | 434 | 4660 |
| BCY 15894 | 392 | nd |
| BCY 15468 | 103 | 1230 |
| BCY 15768 | 44 | 1075 |
| BCY 15769 | 32 | 1120 |

TABLE 6-continued

TfR1 Competition Binding Assay for Selected Peptide Ligands of the Invention

| Peptide Ligand | Human TfR1 Ki (nM) | Cynomolgus TfR1 Ki (nM) |
|---|---|---|
| BCY 15771 | 32 | 1065 |
| BCY 15772 | 926 | 7084 |
| BCY 15773 | 83 | 2301 |
| BCY 15774 | 269 | 3471 |
| BCY 15775 | 6342 | >250 μM |
| BCY 15776 | 1334 | >90 μM |
| BCY 15777 | 2652 | 2910 |
| BCY 15770 | 651 | 4042 |
| BCY 15935 | 300 | nd |
| BCY 15891 | 94 | nd |
| BCY 15939 | 125 | nd |
| BCY 15934 | 63 | nd |
| BCY 15938 | 60 | nd |
| BCY 15937 | 34 | nd |
| BCY 15940 | 54 | nd |
| BCY 17870 | 9 | nd |
| BCY 17871 | 9 | nd |
| BCY 17872 | 14 | nd |
| BCY 17992 | 11 | nd |
| BCY 17993 | 5 | nd |
| BCY 18029 | 6 | nd |
| BCY 18030 | 7 | nd |
| BCY 18031 | 17 | nd |
| BCY 18032 | 77 | nd |
| BCY 18033 | 6 | nd |
| BCY 18034 | 10 | nd |
| BCY 18035 | 17 | nd |
| BCY 18036 | 82 | nd |
| BCY 17873 | 13 | nd |
| BCY 17874 | 13 | nd |
| BCY 17994 | 8 | nd |
| BCY 17995 | 5 | nd |
| BCY 18037 | 11 | nd |
| BCY 18038 | 11 | nd |
| BCY 18039 | 8 | nd |
| BCY 17868 | 23 | nd |
| BCY 17869 | 30 | nd |
| BCY 17875 | 13 | nd |
| BCY 17876 | 16 | nd |
| BCY 17877 | 29 | nd |
| BCY 17878 | 28 | nd |
| BCY 17879 | 32 | nd |
| BCY 17880 | 29 | nd |
| BCY 17109 | 11 | nd |
| BCY 17114 | 32 | nd |
| BCY 17110 | 22 | nd |
| BCY 17111 | 86 | nd |
| BCY 17112 | 47 | nd |
| BCY 17113 | 103 | nd |
| BCY 17115 | 30 | nd |
| BCY 17116 | 75 | nd |
| BCY 17117 | 37 | nd |
| BCY 17118 | 70 | nd |
| BCY 17119 | 160 | nd |
| BCY 17120 | 52 | nd |
| BCY 16048 | 71 | 621 |
| BCY 16049 | 805 | nd |
| BCY 16035 | 91 | nd |
| BCY 16047 | 42 | nd |
| BCY 16039 | 72 | nd |
| BCY 16036 | 127 | nd |
| BCY 16033 | 180 | nd |
| BCY 16038 | 221 | nd |
| BCY 16050 | 473 | nd |
| BCY 16053 | 75 | nd |
| BCY 16089 | 136 | nd |
| BCY 16088 | 161 | nd |
| BCY 16034 | 510 | nd |
| BCY 16037 | 9220 | nd |
| BCY 16045 | 6866 | nd |
| BCY 16046 | 49 | 746 |
| BCY 16051 | 66 | 482 |
| BCY 16041 | 2189 | nd |
| BCY 16042 | 3451 | nd |
| BCY 16031 | 119 | nd |
| BCY 16079 | 123 | nd |
| BCY 16029 | 131 | nd |
| BCY 16052 | 169 | nd |
| BCY 16032 | 654 | nd |
| BCY 16550 | 56 | nd |
| BCY 16753 | 48 | nd |
| BCY 16754 | 18 | nd |
| BCY 16962 | 36 | nd |
| BCY 16963 | 39 | nd |
| BCY 16964 | 52 | nd |
| BCY 16965 | 52 | nd |
| BCY 16966 | 63 | nd |
| BCY 16557 | 37 | nd |
| BCY 16558 | 1623 | nd |
| BCY 17986 | 33 | nd |
| BCY 17987 | 383 (n = 2) | nd |
| BCY 17988 | 213 | nd |
| BCY 17989 | 24 | nd |
| BCY 17990 | 8 | nd |
| BCY 17991 | 3 | nd |
| BCY 17986 | 33 | nd |
| BCY 17988 | 213 | nd |
| BCY 17989 | 24 | nd |
| BCY 17994 | 8 | nd | nd = not determined

5. Transcytosis Assays with TfR1 Binding Bicyclic Peptides in Primary Cultures of Human Proximal Convoluted Cells In order to understand the handling of the TfR1 binding bicyclic peptides, transepithelial fluxes were measured across polarised monolayers of human proximal tubule cell monolayers. Two fluxes JAB (flux in the absorptive direction) and JBA (flux in the secretory direction) were measured over a flux period of 180 minutes. From these fluxes, the net direction (absorption or secretion) and magnitude of TA flux was determined. The experimental details are outlined below:

- The absorptive flux (JAB) and secretory flux (JBA) flux of the TA was determined by applying the compound to either the apical or basolateral side of the confluent monolayer and monitoring the time-resolved distribution of the substrate between the two compartments. From these the net flux (Jnet) was calculated. Bicycle peptides were tested at three concentrations 0.1, 1 and 10 μM.
- Confluent monolayers were paired so that monolayers used for measurement of absorptive flux (JAB) and secretory flux (JBA) had similar TEER values.
- Culture media was aspirated from the insert wells before sequential transfer of the inserts into three beakers of around 100 ml warm modified-Krebs buffer.
- The inserts, with human proximal tubule cell monolayers, were placed in new 24-well plates, each well containing 800 μl warm modified-Krebs buffer of pH 7.4, and 200 μl modified-Krebs buffer of pH 7.4 was added to the insert's upper chamber (apical chamber). The temperature of the experiment was kept at 37° C.
- Prior to the initiation of flux of the Test Articles, monolayers were pre-incubated with Krebs buffer only or Krebs buffer plus vehicle. Monolayers were incubated with Krebs at pH7.4 at either the apical or basolateral membrane as appropriate.

Flux was initiated when the modified-Krebs buffer was aspirated from the apical or basolateral chambers and replaced with equal volume of the required test concentration of the bicyclic peptide at the appropriate pH. This chamber is referred to as the donor chamber. In addition to the bicyclic peptides, Lucifer Yellow with the same concentration of bicyclic peptide was also co-administered to determine the paracellular flux.

Sampling of 50 μl from the contralateral chamber (referred to as the receiver chamber) at predetermined time points after experiment initiation was then carried out. Samples were collected after gentle pipetting twice to mix the buffer.

After each sampling, equal amount of fresh Krebs with the appropriate pH and substrate was replaced. At the last sampling, the reaction was terminated by sequentially transferring the inserts into three beakers of ice-cold Krebs buffer and left to dry.

The 50 μl samples was stored in 96-well PCR plates and spiked with 5.6 μl of 0.1% trifluoroacetic acid (TFA) to give final concentration of 0.01% TFA, before being snap frozen in dry ice for storage.

Monolayers were lysed with 50 μl of 0.01% TFA to determined intracellular amount of bicyclic peptides, and snap frozen as described above.

All samples was stored at −80° C. Samples were submitted for LC-MS/MS determination of bicyclic peptide concentration.

6. Bicyclic Peptide Detection by LC-MS/MS

A total of 648 samples were received for LC-MS/MS analysis.

BCY17986, BCY17988, BCY17989 and BCY17994 were provided individually as 1 mg/mL solutions in DMSO. These were further diluted in acetonitrile/DMSO (50/50, v/v) to make working solutions.

Bulk calibration standards for BCY17986, BCY17988, BCY17989 and BCY17994 in transporter media (modified Krebs buffer), with matrix concentrations ranging from 1.00-1000 nmol/L, were prepared by fortifying transporter media with appropriate amounts of BCY17986, BCY17988, BCY17989 and BCY17994 working solution.

The donor chamber, receiver chamber and lysed kidney cell samples were all quantified using bulk calibration standards and QC samples prepared in transporter media. Any samples which were anticipated to be above the ULOQ on initial analysis were diluted up to 20-fold prior to re-analysis. BCY17986, BCY17988, BCY17989 and BCY17994 were detected in transporter media and lysed kidney cell samples from all test item-dosed in vitro kidney monolayers after dose administration.

Total bicyclic peptide content for each chamber was calculated from the analysed concentrations and corrected for paracellular leak, using the percentage leak of lucifer yellow, to derive true net flux in each direction at each bicyclic peptide concentration. Net fluxes were expressed as pmol/$cm^2$ and plotted against time for apical to basolateral (A-B) and basolateral to apical (B-A) directions.

Figure 2:
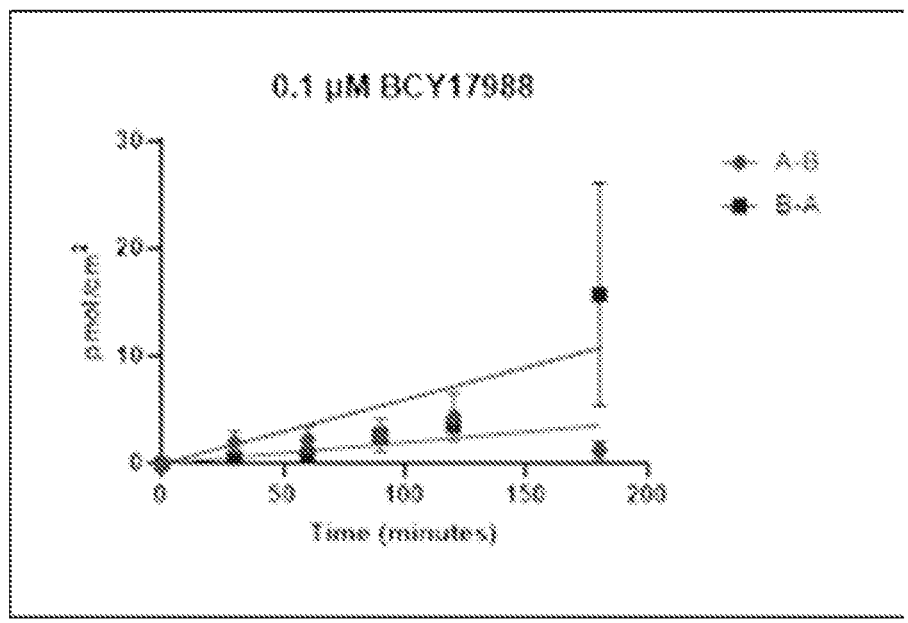
FIG. 2: Results of transcytosis assay with BCY17988 in primary cultures of human proximal convoluted cells.
Figure 2:
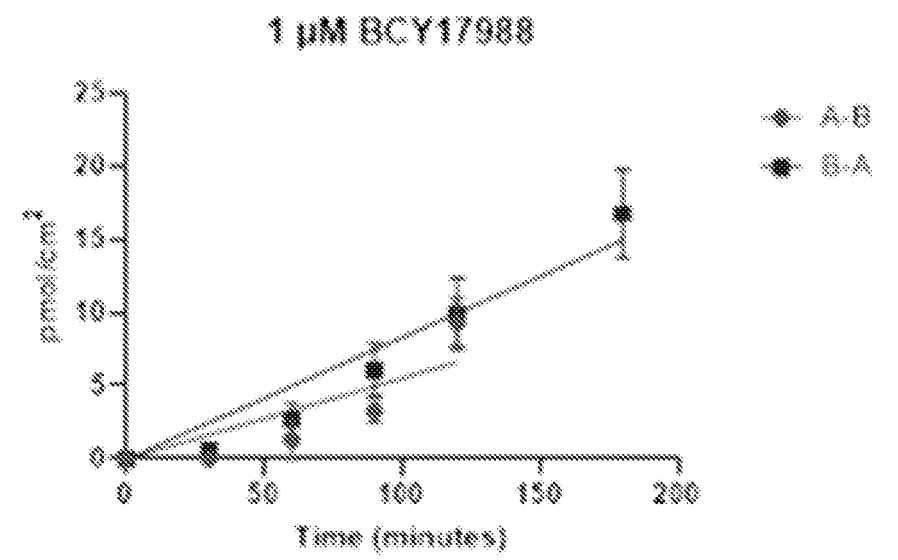
Figure 3:
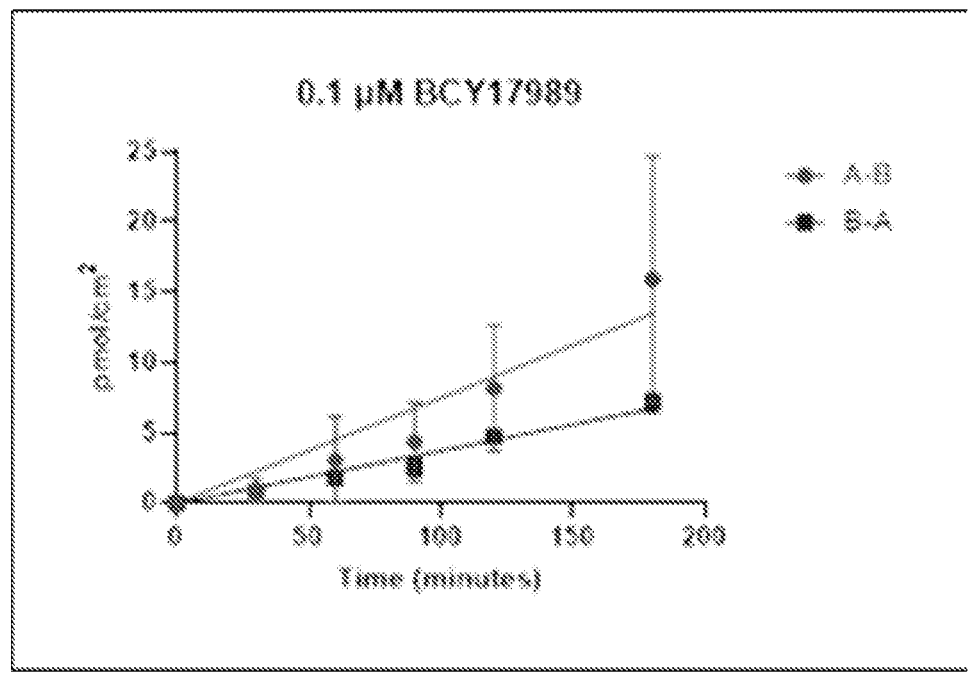
FIG. 3: Results of transcytosis assay with BCY17989 in primary cultures of human proximal convoluted cells.
Figure 3:
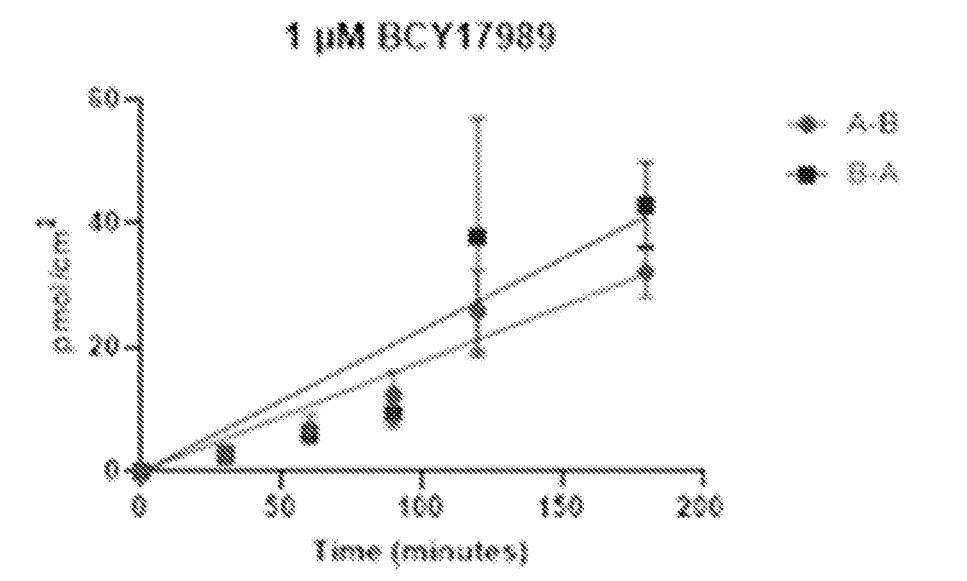
Figure 4:
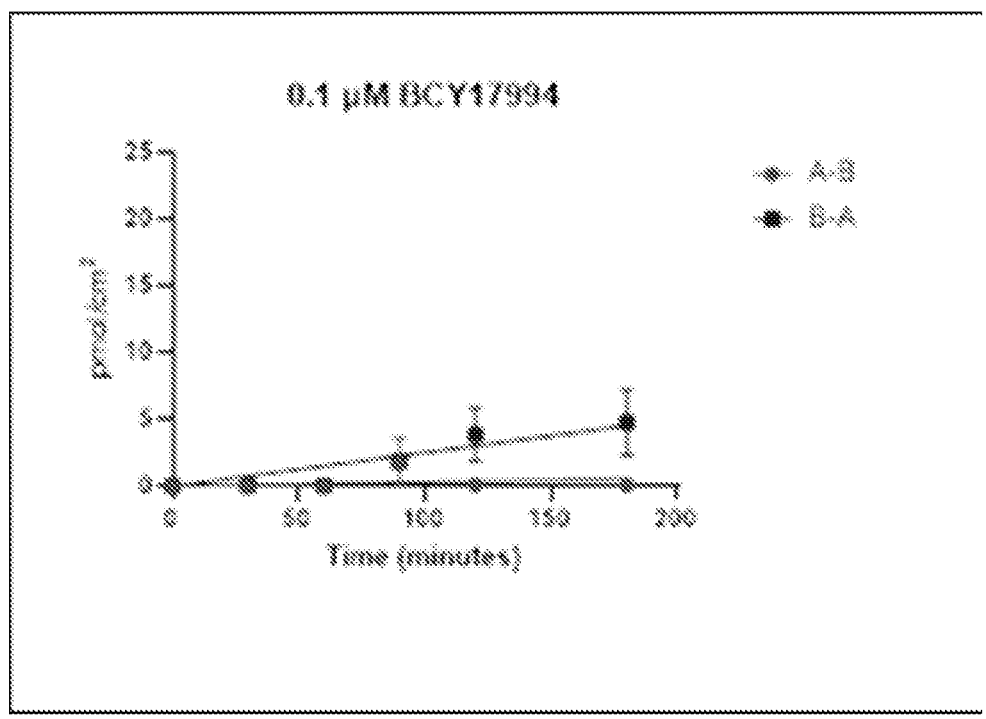
FIG. 4: Results of transcytosis assay with BCY17994 in primary cultures of human proximal convoluted cells.
Figure 4:
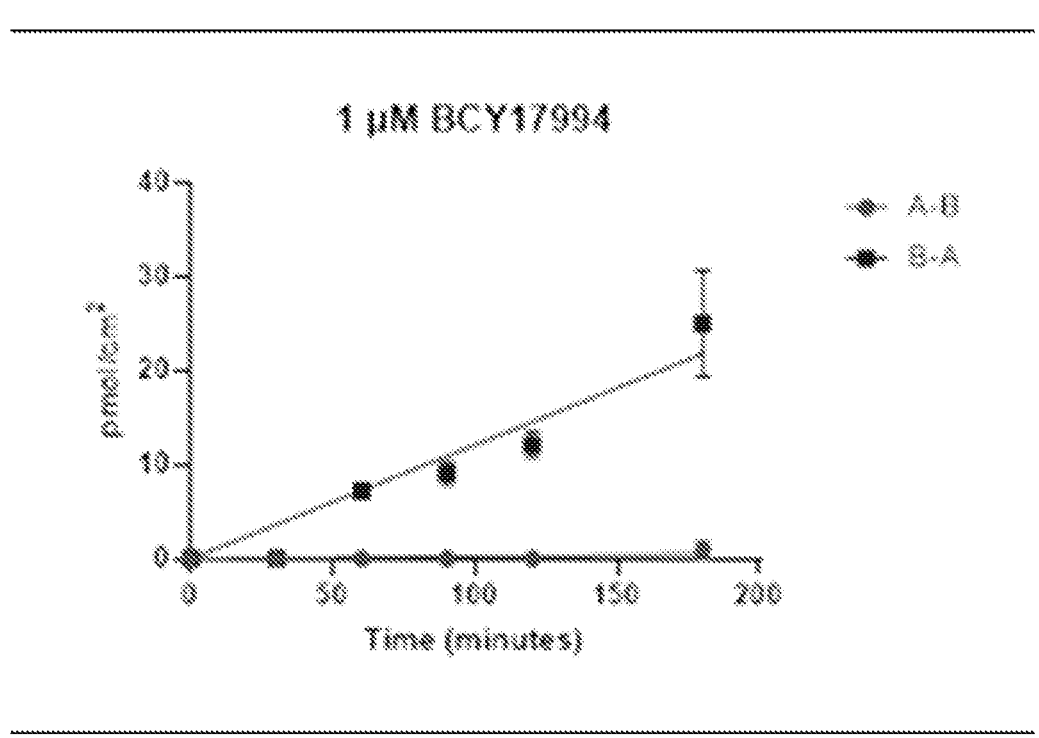

The results of the analysis in sections 5 and 6 above are shown in FIGS. 1 to 4 where it can be seen that all four tested bicyclic peptides showed concentration and time dependent transcytosis in both A-B and B-A direction. This is in agreement with parallel studies which showed binding of FITC transferrin to TfR1 localised on both membranes. Generally Basolateral to Apical flux was greater than Apical to Basolateral. Previous studies have shown internalisation of these bicyclic peptides. This data shows transcytosis of TfR1 binding bicyclic peptides in a human primary culture expressing TfR1, with passage across a polarized cell, indicative of likely transport across endothelial cells of the peripheral and cerebral vasculature.

The invention claimed is:

1. A peptide ligand specific for transferrin receptor 1 (TfR1) comprising a polypeptide comprising at least three reactive groups, separated by at least two loop sequences, and a molecular scaffold which forms covalent bonds with the reactive groups of the polypeptide such that at least two polypeptide loops are formed on the molecular scaffold, wherein said polypeptide comprises an amino acid sequence selected from:

(SEQ ID NO: 1)
$C_i$ALC$_{ii}$NDWTLPWHHC$_{iii}$;

(SEQ ID NO: 2)
$C_i$REFFDTC$_{ii}$GLAFIEC$_{iii}$;

(SEQ ID NO: 3)
$C_i$LEAC$_{ii}$YDGVYWYSC$_{iii}$;

(SEQ ID NO: 4)
$C_i$SADDWLGC$_{ii}$ISWC$_{iii}$;

(SEQ ID NO: 5)
$C_i$SSDAYLGC$_{ii}$ISWC$_{iii}$;

(SEQ ID NO: 6)
$C_i$PPDAHLGC$_{ii}$ISWC$_{iii}$;

-continued (SEQ ID NO: 7)
$C_i$PQDAYLGC$_{ii}$ISWC$_{iii}$;

(SEQ ID NO: 8)
$C_i$PPDSWQGC$_{ii}$ISYC$_{iii}$;

(SEQ ID NO: 9)
$C_i$SPDAHLGC$_{ii}$ISYC$_{iii}$;

(SEQ ID NO: 10)
$C_i$PGDAHLGC$_{ii}$ISYC$_{iii}$;

(SEQ ID NO: 11)
$C_i$PPDSHLGC$_{ii}$ISYC$_{iii}$;

(SEQ ID NO: 12)
$C_i$SADDWLGC$_{ii}$ISYC$_{iii}$;

(SEQ ID NO: 13)
$C_i$P[HyP]DAYLGC$_{ii}$[tBuGly]SYC$_{iii}$;

(SEQ ID NO: 14)
$C_i$P[HyP]DAYLGC$_{ii}$ISYC$_{iii}$;

(SEQ ID NO: 15)
$C_i$S[HyP]DAHLGC$_{ii}$ISYC$_{iii}$;

| | |
|---|---|
| $C_iP[Aib]DAHLGC_{ii}[tBuGly]SYC_{iii}$; | (SEQ ID NO: 16) |
| $C_iPPDAHLGC_{ii}ISYC_{iii}$; | (SEQ ID NO: 17) |
| $C_iP[Aib]DAYLGC_{ii}[tBuGly]SYC_{iii}$; | (SEQ ID NO: 18) |
| $C_iSADAHLGC_{ii}ISYC_{iii}$; | (SEQ ID NO: 19) |
| $C_iS[Aib]DAHLGC_{ii}[tBuGly]SYC_{iii}$; | (SEQ ID NO: 20) |
| $C_iSPDAHLGC_{ii}[EPA]SYC_{iii}$; | (SEQ ID NO: 21) |
| $C_iPPDAYLGC_{ii}[tBuGly]SYC_{iii}$; | (SEQ ID NO: 22) |
| $C_iS[Aib]DAYLGC_{ii}[tBuGly]SYC_{iii}$; | (SEQ ID NO: 23) |
| $C_iAPDAHLGC_{ii}ISYC_{iii}$; | (SEQ ID NO: 24) |
| $C_iP[Aib]DAHLGC_{ii}ISYC_{iii}$; | (SEQ ID NO: 25) |
| $C_iSPDAYLGC_{ii}[tBuGly]SYC_{iii}$; | (SEQ ID NO: 26) |
| $C_iSPDAHLGC_{ii}[tBuGly]SYC_{iii}$; | (SEQ ID NO: 27) |
| $C_iPNDAHLGC_{ii}ISYC_{iii}$; | (SEQ ID NO: 28) |
| $C_iPIDAHLGC_{ii}ISYC_{iii}$; | (SEQ ID NO: 29) |
| $C_iSPDAYLGC_{ii}ISYC_{iii}$; | (SEQ ID NO: 30) |
| $C_iPPDAYLGC_{ii}ISYC_{iii}$; | (SEQ ID NO: 31) |
| $C_iS[Aib]DAHLGC_{ii}ISYC_{iii}$; | (SEQ ID NO: 32) |
| $C_iSPDAHLGC_{ii}[Chg]SYC_{iii}$; | (SEQ ID NO: 33) |
| $C_iAPDAHLGC_{ii}ISYC_{iii}$; | (SEQ ID NO: 34) |
| $C_iYLPDW[tBuAla]C_{ii}GDEYC_{iii}$; | (SEQ ID NO: 35) |
| $C_iSPDAHLGC_{ii}IS[2Nal]C_{iii}$; | (SEQ ID NO: 36) |
| $C_iSPDAHLGC_{ii}IS[3tBuTyr]C_{iii}$; | (SEQ ID NO: 37) |
| $C_iSPD[Aib]HLGC_{ii}ISYC_{iii}$; | (SEQ ID NO: 38) |
| $C_iSPDAHLGC_{ii}IS[1Nal]C_{iii}$; | (SEQ ID NO: 39) |
| $C_iSPDAH[tBuAla]GC_{ii}ISYC_{iii}$; | (SEQ ID NO: 40) |
| $C_iSPDAH[Cba]GC_{ii}ISYC_{iii}$; | (SEQ ID NO: 41) |
| $C_iSPDAHLGC_{ii}ISWC_{iii}$; | (SEQ ID NO: 42) |
| $C_iSPD[Abu]HLGC_{ii}ISYC_{iii}$; | (SEQ ID NO: 43) |
| $C_iS[Aze]DAHLGC_{ii}ISYC_{iii}$; | (SEQ ID NO: 44) |
| $C_iSPDDHLGC_{ii}ISYC_{iii}$; | (SEQ ID NO: 45) |
| $C_iSPDSHLGC_{ii}ISYC_{iii}$; | (SEQ ID NO: 46) |
| $C_iSPDAH[Abu]GC_{ii}ISYC_{iii}$; | (SEQ ID NO: 47) |
| $C_iSPDAHLGC_{ii}IS[4Pal]C_{iii}$; | (SEQ ID NO: 48) |
| $C_iP[dA]DAHLGC_{ii}ISYC_{iii}$; | (SEQ ID NO: 49) |
| $C_iSPDAYLGC_{ii}[tBuAla]SYC_{iii}$; | (SEQ ID NO: 50) |
| $C_iSPDAHLGC_{ii}[C5g]SYC_{iii}$; | (SEQ ID NO: 51) |
| $C_iSPDAHLGC_{ii}[Cbg]SYC_{iii}$; | (SEQ ID NO: 52) |
| $C_iSPDAHL[dA]C_{ii}ISYC_{iii}$; | (SEQ ID NO: 53) |
| $C_iSPDAH[Aib]GC_{ii}ISYC_{iii}$; | (SEQ ID NO: 54) |
| $C_iSPDAHLGC_{ii}[Cpg]SYC_{iii}$; | (SEQ ID NO: 55) |
| $C_iSPDAHLGC_{ii}[B-MeIle]SYC_{iii}$; | (SEQ ID NO: 56) |
| $C_iSADAHLGC_{ii}ISYC_{iii}$; | (SEQ ID NO: 57) |
| $C_iSPAAHLGC_{ii}ISYC_{iii}$; | (SEQ ID NO: 58) |
| $C_iSPDAALGC_{ii}ISYC_{iii}$; | (SEQ ID NO: 59) |
| $C_iSPDAHAGC_{ii}ISYC_{iii}$; | (SEQ ID NO: 60) |
| $C_iSPDAHLAC_{ii}ISYC_{iii}$; | (SEQ ID NO: 61) |
| $C_iSPDAHLGC_{ii}ASYC_{iii}$; | (SEQ ID NO: 62) |
| $C_iSPDAHLGC_{ii}IAYC_{iii}$; | (SEQ ID NO: 63) |
| $C_iSPDAHLGC_{ii}ISAC_{iii}$; | (SEQ ID NO: 64) |
| $C_i[K(N_3)]PDAHLGC_{ii}ISYC_{iii}$; | (SEQ ID NO: 65) |
| $C_iS[K(N_3)]DAHLGC_{ii}ISYC_{iii}$; and | (SEQ ID NO: 66) |
| $C_iSPD[K(N_3)]HLGC_{ii}ISYC_{iii}$; | (SEQ ID NO: 67) | wherein Abu represents aminobutyric acid, Aib represents aminoisobutyric acid, Aze represents azetidine, B-MeIle represents beta-methyl isoleucine, C5g represents cyclopentyl glycine, Cba represents β-cyclobutylalanine, Cbg represents cyclobutyl glycine, Chg represents cyclohexyl glycine, Cpg represents cyclopropryl glycine, EPA represents 2-amino-3-ethyl-pentanoic acid, HyP represents trans-4-hydroxy-L-proline, [K(N₃)] represents 6-azido lysine, 1Nal represents 1-naphthylalanine, 2Nal represents 2-naphthylalanine, 4Pal represents 4-pyridylalanine, tBuAla represents t-butyl-alanine, tBuGly represents t-butyl-glycine, 3tBuTyr represents 3-t-Butyl-tyrosine, and $C_i$, $C_{ii}$, and $C_{iii}$, represent first, second, and third cysteine residues, respectively; or a modified derivative thereof, or a pharmaceutically acceptable salt thereof.

2. The peptide ligand as defined in claim 1, wherein the peptide ligand inhibits the binding of transferrin to TfR1.

3. The peptide ligand as defined in claim 1, wherein said polypeptide comprises an amino acid sequence selected from:

$C_i$ALC$_{ii}$NDWTLPWHHC$_{iii}$; (SEQ ID NO: 1)

$C_i$REFFDTC$_{ii}$GLAFIEC$_{iii}$; (SEQ ID NO: 2)
and $C_i$LEAC$_{ii}$YDGVYWYSC$_{iii}$; (SEQ ID NO: 3)

4. The peptide ligand as defined in claim 1, wherein the peptide ligand does not inhibit the binding of transferrin to TfR1.

5. The peptide ligand as defined in claim 4, wherein said polypeptide comprises an amino acid sequence selected from:

$C_i$SADDWLGC$_{ii}$ISWC$_{iii}$; (SEQ ID NO: 4)

$C_i$SSDAYLGC$_{ii}$ISWC$_{iii}$; (SEQ ID NO: 5)

$C_i$PPDAHLGC$_{ii}$ISWC$_{iii}$; (SEQ ID NO: 6)

$C_i$PQDAYLGC$_{ii}$ISWC$_{iii}$; (SEQ ID NO: 7)

$C_i$PPDSWQGC$_{ii}$ISYC$_{iii}$; (SEQ ID NO: 8)

$C_i$SPDAHLGC$_{ii}$ISYC$_{iii}$; (SEQ ID NO: 9)

$C_i$PGDAHLGC$_{ii}$ISYC$_{iii}$; (SEQ ID NO: 10)

$C_i$PPDSHLGC$_{ii}$ISYC$_{iii}$; (SEQ ID NO: 11)

$C_i$SADDWLGC$_{ii}$ISYC$_{iii}$; (SEQ ID NO: 12)

$C_i$P[HyP]DAYLGC$_{ii}$[tBuGly]SYC$_{iii}$; (SEQ ID NO: 13)

$C_i$P[HyP]DAYLGC$_{ii}$ISYC$_{iii}$; (SEQ ID NO: 14)

$C_i$S[HyP]DAHLGC$_{ii}$ISYC$_{iii}$; (SEQ ID NO: 15)

$C_i$P[Aib]DAHLGC$_{ii}$[tBuGly]SYC$_{iii}$; (SEQ ID NO: 16)

$C_i$PPDAHLGC$_{ii}$ISYC$_{iii}$; (SEQ ID NO: 17)

$C_i$P[Aib]DAYLGC$_{ii}$[tBuGly]SYC$_{iii}$; (SEQ ID NO: 18)

$C_i$SADAHLGC$_{ii}$ISYC$_{iii}$; (SEQ ID NO: 19)

$C_i$S[Aib]DAHLGC$_{ii}$[tBuGly]SYC$_{iii}$; (SEQ ID NO: 20)

$C_i$SPDAHLGC$_{ii}$[EPA]SYC$_{iii}$; (SEQ ID NO: 21)

$C_i$PPDAYLGC$_{ii}$[tBuGly]SYC$_{iii}$; (SEQ ID NO: 22)

$C_i$S[Aib]DAYLGC$_{ii}$[tBuGly]SYC$_{iii}$; (SEQ ID NO: 23)

$C_i$APDAHLGC$_{ii}$ISYC$_{iii}$; (SEQ ID NO: 24)

$C_i$P[Aib]DAHLGC$_{ii}$ISYC$_{iii}$; (SEQ ID NO: 25)

$C_i$SPDAYLGC$_{ii}$[tBuGly]SYC$_{iii}$; (SEQ ID NO: 26)

$C_i$SPDAHLGC$_{ii}$[tBuGly]SYC$_{iii}$; (SEQ ID NO: 27)

$C_i$PNDAHLGC$_{ii}$ISYC$_{iii}$; (SEQ ID NO: 28)

$C_i$PIDAHLGC$_{ii}$ISYC$_{iii}$; (SEQ ID NO: 29)

$C_i$SPDAYLGC$_{ii}$ISYC$_{iii}$; (SEQ ID NO: 30)

$C_i$PPDAYLGC$_{ii}$ISYC$_{iii}$; (SEQ ID NO: 31)

$C_i$S[Aib]DAHLGC$_{ii}$ISYC$_{iii}$; (SEQ ID NO: 32)

$C_i$SPDAHLGC$_{ii}$[Chg]SYC$_{iii}$; (SEQ ID NO: 33)

$C_i$APDAHLGC$_{ii}$ISYC$_{iii}$; (SEQ ID NO: 34)

$C_i$YLPDW[tBuAla]C$_{ii}$GDEYC$_{iii}$; (SEQ ID NO: 35)

$C_i$SPDAHLGC$_{ii}$IS[2Nal]C$_{iii}$; (SEQ ID NO: 36)

$C_i$SPDAHLGC$_{ii}$IS[3tBuTyr]C$_{iii}$; (SEQ ID NO: 37)

$C_i$SPD[Aib]HLGC$_{ii}$ISYC$_{iii}$; (SEQ ID NO: 38)

$C_i$SPDAHLGC$_{ii}$IS[1Nal]C$_{iii}$; (SEQ ID NO: 39)

$C_i$SPDAh[tBuAla]GC$_{ii}$ISYC$_{iii}$; (SEQ ID NO: 40)

$C_i$SPDAH[Cba]GC$_{ii}$ISYC$_{iii}$; (SEQ ID NO: 41)

$C_i$SPDAHLGC$_{ii}$ISWC$_{iii}$; (SEQ ID NO: 42)

$C_i$SPD[Abu]HLGC$_{ii}$ISYC$_{iii}$; (SEQ ID NO: 43)

$C_iS[Aze]DAHLGC_{ii}ISYC_{iii}$; (SEQ ID NO: 44)

$C_iSPDDHLGC_{ii}ISYC_{iii}$; (SEQ ID NO: 45)

$C_iSPDSHLGC_{ii}ISYC_{iii}$; (SEQ ID NO: 46)

$C_iSPDAH[Abu]GC_{ii}ISYC_{iii}$; (SEQ ID NO: 47)

$C_iSPDAHLGC_{ii}ISP[4Pal]C_{iii}$; (SEQ ID NO: 48)

$C_iP[dA]DAHLGC_{ii}ISYC_{iii}$; (SEQ ID NO: 49)

$C_iSPDAYLGC_{ii}[tBuAla]SYC_{iii}$; (SEQ ID NO: 50)

$C_iSPDAHLGC_{ii}[C5g]SYC_{iii}$; (SEQ ID NO: 51)

$C_iSPDAHLGC_{ii}[Cbg]SYC_{iii}$; (SEQ ID NO: 52)

$C_iSPDAHL[dA]C_{ii}ISYC_{iii}$; (SEQ ID NO: 53)

$C_iSPDAH[Aib]GC_{ii}ISYC_{iii}$; (SEQ ID NO: 54)

$C_iSPDAHLGC_{ii}[Cpg]SYC_{iii}$; (SEQ ID NO: 55)

$C_iSPDAHLGC_{ii}[B-MeIle]SYC_{iii}$; (SEQ ID NO: 56)

$C_iSADAHLGC_{ii}ISYC_{iii}$; (SEQ ID NO: 57)

$C_iSPAAHLGC_{ii}ISYC_{iii}$; (SEQ ID NO: 58)

$C_iSPDAALGC_{ii}ISYC_{iii}$; (SEQ ID NO: 59)

$C_iSPDAHAGC_{ii}ISYC_{iii}$; (SEQ ID NO: 60)

$C_iSPDAHLAC_{ii}ISYC_{iii}$; (SEQ ID NO: 61)

$C_iSPDAHLGC_{ii}ASYC_{iii}$; (SEQ ID NO: 62)

$C_iSPDAHLGC_{ii}IAYC_{iii}$; (SEQ ID NO: 63)

$C_iSPDAHLGC_{ii}ISAC_{iii}$; (SEQ ID NO: 64)

$C_i[K(N_3)]PDAHLGC_{ii}ISYC_{iii}$; (SEQ ID NO: 65)

$C_iS[K(N_3)]DAHLGC_{ii}ISYC_{iii}$; and (SEQ ID NO: 66)

$C_iSPD[K(N_3)]HLGC_{ii}ISYC_{iii}$; (SEQ ID NO: 67)

6. The peptide ligand as defined in claim 1, wherein the peptide ligand is in the form of a free acid.

7. A multimeric binding complex which comprises at least two of the peptide ligands according to claim 1.

8. The multimeric binding complex according to claim 7, wherein the complex comprises 2 to 10 peptide ligands attaching to a central moiety.

9. The multimeric binding complex according to claim 8, wherein the complex comprises 2 peptide ligands attaching to a central moiety of formula (A):

10. A pharmaceutical composition comprising the peptide ligand as defined in claim 1, in combination with one or more pharmaceutically acceptable excipients.

11. A tissue delivery complex which comprises the peptide ligand as defined in claim 1, bound to TfR1 in combination with a payload.

12. The tissue delivery complex as defined in claim 11, wherein the payload is an oligonucleotide.

13. A pharmaceutical composition comprising the multimeric binding complex as defined in claim 7, in combination with one or more pharmaceutically acceptable excipients.

14. A tissue delivery complex which comprises the multimeric binding complex as defined in claim 7, bound to TfR1 in combination with a payload.

15. The peptide ligand as defined in claim 1, wherein the molecular scaffold is 1,1',1"-(1,3,5-triazinane-1,3,5-triyl) triprop-2-en-1-one (TATA).

16. The peptide ligand as defined in claim 1, wherein the pharmaceutically acceptable salt is selected from a sodium salt, a potassium salt, a calcium salt, and an ammonium salt.

17. The peptide ligand as defined in claim 1, wherein the molecular scaffold is 1,1',1"-(1,3,5-triazinane-1,3,5-triyl)tris (2-bromoethanone) (TATB).

18. The peptide ligand as defined in claim 1, wherein the molecular scaffold is 1,1',1''-(1,3,5-triazinane-1,3,5-triyl) triprop-2-en-1-one (TATA), and said polypeptide comprises an amino acid sequence selected from:
- A-(SEQ ID NO: 1)-A (herein referred to as BCY12455);
- A-(SEQ ID NO: 1)-A-[Sar$_6$]-[K-Fl] (herein referred to as BCY12652);
- A-(SEQ ID NO: 2)-A (herein referred to as BCY12452);
- A-(SEQ ID NO: 2)-A-[Sar$_6$]-[K-Fl] (herein referred to as BCY12650);
- A-(SEQ ID NO: 3)-A (herein referred to as BCY12454); and
- A-(SEQ ID NO: 3)-A-[Sar$_6$]-[K-Fl] (herein referred to as BCY12651);

wherein Sar represents sarcosine and Fl represents fluorescein.

19. The peptide ligand as defined in claim 1, wherein the molecular scaffold is 1,1',1''-(1,3,5-triazinane-1,3,5-triyl)tris (2-bromoethanone) (TATB), and said polypeptide comprises an amino acid sequence selected from:
- A-(SEQ ID NO: 4)-A (herein referred to as BCY13983);
- A-(SEQ ID NO: 4)-A-[Sar$_6$]-[K-Fl] (herein referred to as BCY14474);
- A-(SEQ ID NO: 5)-A (herein referred to as BCY13986);
- A-(SEQ ID NO: 5)-A-[Sar$_6$]-[K-Fl] (herein referred to as BCY14475);
- A-(SEQ ID NO: 6)-A (herein referred to as BCY15466);
- Ac-(SEQ ID NO: 6) (herein referred to as BCY15889);
- A-(SEQ ID NO: 7)-A (herein referred to as BCY15467);
- Ac-(SEQ ID NO: 7) (herein referred to as BCY15890);
- A-(SEQ ID NO: 8)-A (herein referred to as BCY13989);
- A-(SEQ ID NO: 8)-A-[Sar$_6$]-[K-Fl] (herein referred to as BCY14476);
- A-(SEQ ID NO: 9)-A (herein referred to as BCY15468);
- A-(SEQ ID NO: 9)-A-[Sar$_6$]-[K-Fl] (herein referred to as BCY15768);
- (SEQ ID NO: 9)-[Sar$_6$]-[K-Fl] (herein referred to as BCY15934);
- Ac-(SEQ ID NO: 9)-A-[Sar$_6$]-[K-Fl] (herein referred to as BCY15937);
- Ac-(SEQ ID NO: 9)-[Sar$_6$]-[K-Fl] (herein referred to as BCY15938);
- [Fl]G[Sar$_5$]-A-(SEQ ID NO: 9)-A (herein referred to as BCY15940);
- N[1Nal]N-(SEQ ID NO: 9) (herein referred to as BCY18030);
- Ac-(SEQ ID NO: 9)-E[Pip]W (herein referred to as BCY18039);
- Ac-(SEQ ID NO: 9)-EPW (herein referred to as BCY17994);
- NWN-(SEQ ID NO: 9) (herein referred to as BCY18029);
- NWN-(SEQ ID NO: 9)-A (herein referred to as BCY17109);
- Ac-(SEQ ID NO: 9)-E[Aze]W (herein referred to as BCY18037);
- Ac-NWN-(SEQ ID NO: 9) (herein referred to as BCY17992);
- Ac-(SEQ ID NO: 9)-E[dP]W (herein referred to as BCY18038);
- Ac-N[1Nal]N-(SEQ ID NO: 9) (herein referred to as BCY18034);
- N[dW]N-(SEQ ID NO: 9) (herein referred to as BCY18031);
- Ac-N[dW]N-(SEQ ID NO: 9) (herein referred to as BCY18035);
- HWM-(SEQ ID NO: 9)-A (herein referred to as BCY17110);
- A-(SEQ ID NO: 9)-PHP (herein referred to as BCY17115);
- A-(SEQ ID NO: 9)-EPW (herein referred to as BCY17114);
- NEV-(SEQ ID NO: 9)-A (herein referred to as BCY17112);
- A-(SEQ ID NO: 9)-PIVH (herein referred to as BCY17120);
- Ac-(SEQ ID NO: 9) (herein referred to as BCY15891);
- HTS-(SEQ ID NO: 9)-A (herein referred to as BCY17111);
- Ac-N[NMeTrp]N-(SEQ ID NO: 9) (herein referred to as BCY18036);
- N[NMeTrp]N-(SEQ ID NO: 9) (herein referred to as BCY18032);
- Ac-A-(SEQ ID NO: 9)-A (herein referred to as BCY15939);
- A-(SEQ ID NO: 9)-EHQE (herein referred to as BCY17119);
- ESF-(SEQ ID NO: 9)-A (herein referred to as BCY17113);
- NWN-(SEQ ID NO: 9)-[K(N$_3$)] (herein referred to as BCY17870);
- Ac-NWN-(SEQ ID NO: 9)-[K(N$_3$)] (herein referred to as BCY17871);
- [AzPro]-NWN-(SEQ ID NO: 9) (herein referred to as BCY17872);
- Ac-(SEQ ID NO: 9)-EPW-[K(N$_3$)] (herein referred to as BCY17873);
- [AzPro]-(SEQ ID NO: 9)-EPW (herein referred to as BCY17874);
- Ac-(SEQ ID NO: 9)-[K(N$_3$)] (herein referred to as BCY17868);
- [AzPro]-(SEQ ID NO: 9) (herein referred to as BCY17869);
- Ac-N[dY]N-(SEQ ID NO: 9)-[K(N$_3$)] (herein referred to as BCY17882);
- Ac-(SEQ ID NO: 9)-E-[dP]-W-[K(N$_3$)] (herein referred to as BCY17890);
- Ac-(SEQ ID NO: 9)-E-[Aze]-W-[K(N$_3$)] (herein referred to as BCY17892);
- Ac-(SEQ ID NO: 9)-E-[Pip]-W-[K(N$_3$)] (herein referred to as BCY17894);
- Ac-(SEQ ID NO: 9)-[K(N$_3$)(PYA-maleimide] (herein referred to as BCY17906);
- Ac-(SEQ ID NO: 9)-EPW-[Peg$_{10}$]-[K(N$_3$)] (herein referred to as BCY19405);
- Ac-(SEQ ID NO: 9)-EPW-[Peg$_{24}$]-[K(N$_3$)] (herein referred to as BCY19406);
- Ac-(SEQ ID NO: 9)-EPWGGSGGS-[K(N$_3$)] (herein referred to as BCY19407);
- A-(SEQ ID NO: 10)-A (herein referred to as BCY15469);
- Ac-(SEQ ID NO: 10) (herein referred to as BCY15892);
- A-(SEQ ID NO: 11)-A (herein referred to as BCY15470);
- Ac-(SEQ ID NO: 11) (herein referred to as BCY15893);
- A-(SEQ ID NO: 12)-A (herein referred to as BCY15471);
- Ac-(SEQ ID NO: 12) (herein referred to as BCY15894);
- Ac-(SEQ ID NO: 13) (herein referred to as BCY17991);
- Ac-(SEQ ID NO: 13)-EPW (herein referred to as BCY17995);
- Ac-NWN-(SEQ ID NO: 13) (herein referred to as BCY17993);
- NWN-(SEQ ID NO: 13) (herein referred to as BCY18033);
- A-(SEQ ID NO: 13)-A (herein referred to as BCY16754);
- Ac-(SEQ ID NO: 13)-[K(N$_3$)] (herein referred to as BCY17896);

Ac-NWN-(SEQ ID NO: 13)-[K(N₃)] (herein referred to as BCY17899);
Ac-(SEQ ID NO: 13)-EPW-[K(N₃)] (herein referred to as BCY17901);
Ac-(SEQ ID NO: 14) (herein referred to as BCY17990);
Ac-(SEQ ID NO: 14)-[K(N₃)] (herein referred to as BCY17875);
[AzPro]-(SEQ ID NO: 14) (herein referred to as BCY17876);
Ac-(SEQ ID NO: 15) (herein referred to as BCY17989);
A-(SEQ ID NO: 15)-A (herein referred to as BCY16047);
Ac-(SEQ ID NO: 15)-[K(N₃)] (herein referred to as BCY17877);
[AzPro]-(SEQ ID NO: 15) (herein referred to as BCY17878);
A-(SEQ ID NO: 16)-A (herein referred to as BCY16962);
TYMN-(SEQ ID NO: 17)-A (herein referred to as BCY17117);
A-(SEQ ID NO: 17)-A (herein referred to as BCY16048);
A-(SEQ ID NO: 18)-A (herein referred to as BCY16963);
Ac-(SEQ ID NO: 19) (herein referred to as BCY17987);
A-(SEQ ID NO: 20)-A (herein referred to as BCY16753);
A-(SEQ ID NO: 21)-A (herein referred to as BCY16046);
A-(SEQ ID NO: 22)-A (herein referred to as BCY16964);
A-(SEQ ID NO: 23)-A (herein referred to as BCY16965);
Ac-(SEQ ID NO: 24) (herein referred to as BCY17986);
A-(SEQ ID NO: 25)-A (herein referred to as BCY16550);
A-(SEQ ID NO: 26)-A (herein referred to as BCY16966);
A-(SEQ ID NO: 27)-A (herein referred to as BCY16051);
IDSN-(SEQ ID NO: 28)-A (herein referred to as BCY17118);
WGKS-(SEQ ID NO: 29)-A (herein referred to as BCY17116);
A-(SEQ ID NO: 30)-A (herein referred to as BCY16053);
A-(SEQ ID NO: 31)-A (herein referred to as BCY16557);
A-(SEQ ID NO: 32)-A (herein referred to as BCY16035);
A-(SEQ ID NO: 33)-A (herein referred to as BCY16043);
A-(SEQ ID NO: 34)-A-[Sar₆]-[K-Fl] (herein referred to as BCY15769);
A-(SEQ ID NO: 35)-A (herein referred to as BCY15648);
A-(SEQ ID NO: 36)-A (herein referred to as BCY16031);
A-(SEQ ID NO: 37)-A (herein referred to as BCY16079);
A-(SEQ ID NO: 38)-A (herein referred to as BCY16036);
A-(SEQ ID NO: 39)-A (herein referred to as BCY16029);
A-(SEQ ID NO: 40)-A (herein referred to as BCY16089);
A-(SEQ ID NO: 41)-A (herein referred to as BCY16088);
A-(SEQ ID NO: 42)-A (herein referred to as BCY16052);
A-(SEQ ID NO: 43)-A (herein referred to as BCY16033);
A-(SEQ ID NO: 44)-A (herein referred to as BCY16039);
Ac-(SEQ ID NO: 44) (herein referred to as BCY17988);
Ac-(SEQ ID NO: 44)-[K(N₃)] (herein referred to as BCY17879);
[AzPro]-(SEQ ID NO: 44) (herein referred to as BCY17880);
A-(SEQ ID NO: 45)-A (herein referred to as BCY16038);
A-(SEQ ID NO: 46)-A (herein referred to as BCY16050);
A-(SEQ ID NO: 47)-A (herein referred to as BCY16034);
A-(SEQ ID NO: 48)-A (herein referred to as BCY16032);
A-(SEQ ID NO: 49)-A (herein referred to as BCY16049);
A-(SEQ ID NO: 50)-A (herein referred to as BCY16558);
A-(SEQ ID NO: 51)-A (herein referred to as BCY16041);
A-(SEQ ID NO: 52)-A (herein referred to as BCY16042);
A-(SEQ ID NO: 53)-A (herein referred to as BCY16045);
A-(SEQ ID NO: 54)-A (herein referred to as BCY16037);
A-(SEQ ID NO: 55)-A (herein referred to as BCY16044);
A-(SEQ ID NO: 56)-A (herein referred to as BCY16040);
A-(SEQ ID NO: 57)-A-[Sar₆]-[K-Fl] (herein referred to as BCY15771);
A-(SEQ ID NO: 58)-A-[Sar₆]-[K-Fl] (herein referred to as BCY15772);
A-(SEQ ID NO: 59)-A-[Sar₆]-[K-Fl] (herein referred to as BCY15773);
A-(SEQ ID NO: 60)-A-[Sar₆]-[K-Fl] (herein referred to as BCY15774);
A-(SEQ ID NO: 61)-A-[Sar₆]-[K-Fl] (herein referred to as BCY15775);
A-(SEQ ID NO: 62)-A-[Sar₆]-[K-Fl] (herein referred to as BCY15776);
A-(SEQ ID NO: 63)-A-[Sar₆]-[K-Fl] (herein referred to as BCY15777);
A-(SEQ ID NO: 64)-A-[Sar₆]-[K-Fl] (herein referred to as BCY15770);
Ac-(SEQ ID NO: 65) (herein referred to as BCY17903);
Ac-(SEQ ID NO: 66) (herein referred to as BCY17904); and
Ac-(SEQ ID NO: 67) (herein referred to as BCY17905);
wherein AzPro represents azidopropyl, Aze represents azetidine, 1Nal represents 1-naphthylalanine, NMeTrp represents N-methyl-tryptophan, [K(N₃)] represents 6-azido lysine, Peg represents polyethylene glycol, Pip represents pipecolic acid, Sar represents sarcosine, Fl represents fluorescein and [K(N₃)(PYA-Maleimide)] represents a modified lysine having a structure:

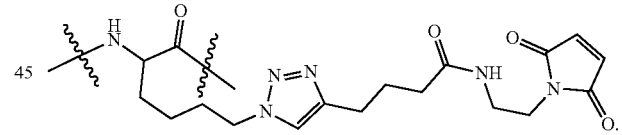

20. The peptide ligand as defined in claim 1, wherein the molecular scaffold is 1,1',1''-(1,3,5-triazinane-1,3,5-triyl)triprop-2-en-1-one (TATA), and said polypeptide comprises an amino acid sequence: Ac-(SEQ ID NO: 13) (herein referred to as BCY20546).

* * * * *

SEQUENCE LISTING

```
<160> NUMBER OF SEQ ID NOS: 67

<210> SEQ ID NO 1
<211> LENGTH: 14
<212> TYPE: PRT
<213> ORGANISM: Artificial
<220> FEATURE:
<223> OTHER INFORMATION: Synthetic Peptide

<400> SEQUENCE: 1

Cys Ala Leu Cys Asn Asp Trp Thr Leu Pro Trp His His Cys
1               5                   10

<210> SEQ ID NO 2
<211> LENGTH: 15
<212> TYPE: PRT
<213> ORGANISM: Artificial
<220> FEATURE:
<223> OTHER INFORMATION: Synthetic Peptide

<400> SEQUENCE: 2

Cys Arg Glu Phe Phe Asp Thr Cys Gly Leu Ala Phe Ile Glu Cys
1               5                   10                  15

<210> SEQ ID NO 3
<211> LENGTH: 14
<212> TYPE: PRT
<213> ORGANISM: Artificial
<220> FEATURE:
```

<223> OTHER INFORMATION: Synthetic Peptide

<400> SEQUENCE: 3

Cys Leu Glu Ala Cys Tyr Asp Gly Val Tyr Trp Tyr Ser Cys
1               5                   10

<210> SEQ ID NO 4
<211> LENGTH: 13
<212> TYPE: PRT
<213> ORGANISM: Artificial
<220> FEATURE:
<223> OTHER INFORMATION: Synthetic Peptide

<400> SEQUENCE: 4

Cys Ser Ala Asp Asp Trp Leu Gly Cys Ile Ser Trp Cys
1               5                   10

<210> SEQ ID NO 5
<211> LENGTH: 13
<212> TYPE: PRT
<213> ORGANISM: Artificial
<220> FEATURE:
<223> OTHER INFORMATION: Synthetic Peptide

<400> SEQUENCE: 5

Cys Ser Ser Asp Ala Tyr Leu Gly Cys Ile Ser Trp Cys
1               5                   10

<210> SEQ ID NO 6
<211> LENGTH: 13
<212> TYPE: PRT
<213> ORGANISM: Artificial
<220> FEATURE:
<223> OTHER INFORMATION: Synthetic Peptide

<400> SEQUENCE: 6

Cys Pro Pro Asp Ala His Leu Gly Cys Ile Ser Trp Cys
1               5                   10

<210> SEQ ID NO 7
<211> LENGTH: 13
<212> TYPE: PRT
<213> ORGANISM: Artificial
<220> FEATURE:
<223> OTHER INFORMATION: Synthetic Peptide

<400> SEQUENCE: 7

Cys Pro Gln Asp Ala Tyr Leu Gly Cys Ile Ser Trp Cys
1               5                   10

<210> SEQ ID NO 8
<211> LENGTH: 13
<212> TYPE: PRT
<213> ORGANISM: Artificial
<220> FEATURE:
<223> OTHER INFORMATION: Synthetic Peptide

<400> SEQUENCE: 8

Cys Pro Pro Asp Ser Trp Gln Gly Cys Ile Ser Tyr Cys
1               5                   10

<210> SEQ ID NO 9
<211> LENGTH: 13
<212> TYPE: PRT
<213> ORGANISM: Artificial
<220> FEATURE:
<223> OTHER INFORMATION: Synthetic Peptide

<400> SEQUENCE: 9

Cys Ser Pro Asp Ala His Leu Gly Cys Ile Ser Tyr Cys
1               5                   10

<210> SEQ ID NO 10
<211> LENGTH: 13
<212> TYPE: PRT
<213> ORGANISM: Artificial
<220> FEATURE:
<223> OTHER INFORMATION: Synthetic Peptide

<400> SEQUENCE: 10

Cys Pro Gly Asp Ala His Leu Gly Cys Ile Ser Tyr Cys
1               5                   10

<210> SEQ ID NO 11
<211> LENGTH: 13
<212> TYPE: PRT
<213> ORGANISM: Artificial
<220> FEATURE:
<223> OTHER INFORMATION: Synthetic Peptide

<400> SEQUENCE: 11

Cys Pro Pro Asp Ser His Leu Gly Cys Ile Ser Tyr Cys
1               5                   10

<210> SEQ ID NO 12
<211> LENGTH: 13
<212> TYPE: PRT
<213> ORGANISM: Artificial
<220> FEATURE:
<223> OTHER INFORMATION: Synthetic Peptide

<400> SEQUENCE: 12

Cys Ser Ala Asp Asp Trp Leu Gly Cys Ile Ser Tyr Cys
1               5                   10

<210> SEQ ID NO 13
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is HyP
<220> FEATURE:
<221> NAME/KEY: Xaa
<222> LOCATION: (10)..(10)
<223> OTHER INFORMATION: Xaa is tBuGly

<400> SEQUENCE: 13

Cys Pro Xaa Asp Ala Tyr Leu Gly Cys Xaa Ser Tyr Cys
1               5                   10

<210> SEQ ID NO 14
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is HyP

<400> SEQUENCE: 14

Cys Pro Xaa Asp Ala Tyr Leu Gly Cys Ile Ser Tyr Cys
1               5                   10

<210> SEQ ID NO 15
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is HyP

<400> SEQUENCE: 15

Cys Ser Xaa Asp Ala His Leu Gly Cys Ile Ser Tyr Cys
1               5                   10

<210> SEQ ID NO 16
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Aib
<220> FEATURE:
<221> NAME/KEY: Xaa
<222> LOCATION: (10)..(10)
<223> OTHER INFORMATION: Xaa is tBuGly

<400> SEQUENCE: 16

Cys Pro Xaa Asp Ala His Leu Gly Cys Xaa Ser Tyr Cys
1               5                   10

<210> SEQ ID NO 17
<211> LENGTH: 13
<212> TYPE: PRT
<213> ORGANISM: Artificial
<220> FEATURE:
<223> OTHER INFORMATION: Synthetic Peptide

<400> SEQUENCE: 17

Cys Pro Pro Asp Ala His Leu Gly Cys Ile Ser Tyr Cys
1               5                   10

<210> SEQ ID NO 18
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Aib
<220> FEATURE:
<221> NAME/KEY: Xaa
<222> LOCATION: (10)..(10)
<223> OTHER INFORMATION: Xaa is tBuGly

<400> SEQUENCE: 18

Cys Pro Xaa Asp Ala Tyr Leu Gly Cys Xaa Ser Tyr Cys
1               5                   10

<210> SEQ ID NO 19
<211> LENGTH: 13

```
<212> TYPE: PRT
<213> ORGANISM: Artificial
<220> FEATURE:
<223> OTHER INFORMATION: Synthetic Peptide

<400> SEQUENCE: 19

Cys Ser Ala Asp Ala His Leu Gly Cys Ile Ser Tyr Cys
1               5                   10

<210> SEQ ID NO 20
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Aib
<220> FEATURE:
<221> NAME/KEY: Xaa
<222> LOCATION: (10)..(10)
<223> OTHER INFORMATION: Xaa is tBuGly

<400> SEQUENCE: 20

Cys Ser Xaa Asp Ala His Leu Gly Cys Xaa Ser Tyr Cys
1               5                   10

<210> SEQ ID NO 21
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is EPA

<400> SEQUENCE: 21

Cys Ser Pro Asp Ala His Leu Gly Cys Xaa Ser Tyr Cys
1               5                   10

<210> SEQ ID NO 22
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is tBuGly

<400> SEQUENCE: 22

Cys Pro Pro Asp Ala Tyr Leu Gly Cys Xaa Ser Tyr Cys
1               5                   10

<210> SEQ ID NO 23
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Aib
<220> FEATURE:
<221> NAME/KEY: Xaa
<222> LOCATION: (10)..(10)
```

<223> OTHER INFORMATION: Xaa is tBuGly

<400> SEQUENCE: 23

Cys Ser Xaa Asp Ala Tyr Leu Gly Cys Xaa Ser Tyr Cys
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic Peptide

<400> SEQUENCE: 24

Cys Ala Pro Asp Ala His Leu Gly Cys Ile Ser Tyr Cys
1               5                   10

<210> SEQ ID NO 25
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Aib

<400> SEQUENCE: 25

Cys Pro Xaa Asp Ala His Leu Gly Cys Ile Ser Tyr Cys
1               5                   10

<210> SEQ ID NO 26
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is tBuGly

<400> SEQUENCE: 26

Cys Ser Pro Asp Ala Tyr Leu Gly Cys Xaa Ser Tyr Cys
1               5                   10

<210> SEQ ID NO 27
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is tBuGly

<400> SEQUENCE: 27

Cys Ser Pro Asp Ala His Leu Gly Cys Xaa Ser Tyr Cys
1               5                   10

<210> SEQ ID NO 28
<211> LENGTH: 13
<212> TYPE: PRT
<213> ORGANISM: Artificial
<220> FEATURE:
<223> OTHER INFORMATION: Synthetic Peptide

<400> SEQUENCE: 28

Cys Pro Asn Asp Ala His Leu Gly Cys Ile Ser Tyr Cys
1               5                   10

<210> SEQ ID NO 29
<211> LENGTH: 13
<212> TYPE: PRT
<213> ORGANISM: Artificial
<220> FEATURE:
<223> OTHER INFORMATION: Synthetic Peptide

<400> SEQUENCE: 29

Cys Pro Ile Asp Ala His Leu Gly Cys Ile Ser Tyr Cys
1               5                   10

<210> SEQ ID NO 30
<211> LENGTH: 13
<212> TYPE: PRT
<213> ORGANISM: Artificial
<220> FEATURE:
<223> OTHER INFORMATION: Synthetic Peptide

<400> SEQUENCE: 30

Cys Ser Pro Asp Ala Tyr Leu Gly Cys Ile Ser Tyr Cys
1               5                   10

<210> SEQ ID NO 31
<211> LENGTH: 13
<212> TYPE: PRT
<213> ORGANISM: Artificial
<220> FEATURE:
<223> OTHER INFORMATION: Synthetic Peptide

<400> SEQUENCE: 31

Cys Pro Pro Asp Ala Tyr Leu Gly Cys Ile Ser Tyr Cys
1               5                   10

<210> SEQ ID NO 32
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Aib

<400> SEQUENCE: 32

Cys Ser Xaa Asp Ala His Leu Gly Cys Ile Ser Tyr Cys
1               5                   10

<210> SEQ ID NO 33
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is Chg

<400> SEQUENCE: 33

Cys Ser Pro Asp Ala His Leu Gly Cys Xaa Ser Tyr Cys
1               5                   10

-continued

```
<210> SEQ ID NO 34
<211> LENGTH: 13
<212> TYPE: PRT
<213> ORGANISM: Artificial
<220> FEATURE:
<223> OTHER INFORMATION: Synthetic Peptide

<400> SEQUENCE: 34

Cys Ala Pro Asp Ala His Leu Gly Cys Ile Ser Tyr Cys
1               5                   10

<210> SEQ ID NO 35
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is tBuAla

<400> SEQUENCE: 35

Cys Tyr Leu Pro Asp Trp Xaa Cys Gly Asp Glu Tyr Cys
1               5                   10

<210> SEQ ID NO 36
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (12)..(12)
<223> OTHER INFORMATION: Xaa is 2Nal

<400> SEQUENCE: 36

Cys Ser Pro Asp Ala His Leu Gly Cys Ile Ser Xaa Cys
1               5                   10

<210> SEQ ID NO 37
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (12)..(12)
<223> OTHER INFORMATION: Xaa is 3tBuTyr

<400> SEQUENCE: 37

Cys Ser Pro Asp Ala His Leu Gly Cys Ile Ser Xaa Cys
1               5                   10

<210> SEQ ID NO 38
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is Aib

<400> SEQUENCE: 38

Cys Ser Pro Asp Xaa His Leu Gly Cys Ile Ser Tyr Cys
1               5                   10
```

```
<210> SEQ ID NO 39
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (12)..(12)
<223> OTHER INFORMATION: Xaa is 1Nal

<400> SEQUENCE: 39

Cys Ser Pro Asp Ala His Leu Gly Cys Ile Ser Xaa Cys
1               5                   10

<210> SEQ ID NO 40
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is tBuAla

<400> SEQUENCE: 40

Cys Ser Pro Asp Ala His Xaa Gly Cys Ile Ser Tyr Cys
1               5                   10

<210> SEQ ID NO 41
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is Cba

<400> SEQUENCE: 41

Cys Ser Pro Asp Ala His Xaa Gly Cys Ile Ser Tyr Cys
1               5                   10

<210> SEQ ID NO 42
<211> LENGTH: 13
<212> TYPE: PRT
<213> ORGANISM: Artificial
<220> FEATURE:
<223> OTHER INFORMATION: Synthetic Peptide

<400> SEQUENCE: 42

Cys Ser Pro Asp Ala His Leu Gly Cys Ile Ser Trp Cys
1               5                   10

<210> SEQ ID NO 43
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is Abu

<400> SEQUENCE: 43
```

```
Cys Ser Pro Asp Xaa His Leu Gly Cys Ile Ser Tyr Cys
1               5                   10
```

<210> SEQ ID NO 44
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is Aze

<400> SEQUENCE: 44

```
Cys Ser Xaa Asp Ala His Leu Gly Cys Ile Ser Tyr Cys
1               5                   10
```

<210> SEQ ID NO 45
<211> LENGTH: 13
<212> TYPE: PRT
<213> ORGANISM: Artificial
<220> FEATURE:
<223> OTHER INFORMATION: Synthetic Peptide

<400> SEQUENCE: 45

```
Cys Ser Pro Asp Asp His Leu Gly Cys Ile Ser Tyr Cys
1               5                   10
```

<210> SEQ ID NO 46
<211> LENGTH: 13
<212> TYPE: PRT
<213> ORGANISM: Artificial
<220> FEATURE:
<223> OTHER INFORMATION: Synthetic Peptide

<400> SEQUENCE: 46

```
Cys Ser Pro Asp Ser His Leu Gly Cys Ile Ser Tyr Cys
1               5                   10
```

<210> SEQ ID NO 47
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is Abu

<400> SEQUENCE: 47

```
Cys Ser Pro Asp Ala His Xaa Gly Cys Ile Ser Tyr Cys
1               5                   10
```

<210> SEQ ID NO 48
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (12)..(12)
<223> OTHER INFORMATION: Xaa is 4Pal

<400> SEQUENCE: 48

```
Cys Ser Pro Asp Ala His Leu Gly Cys Ile Ser Xaa Cys
1               5                   10
```

```
<210> SEQ ID NO 49
<211> LENGTH: 13
<212> TYPE: PRT
<213> ORGANISM: Artificial
<220> FEATURE:
<223> OTHER INFORMATION: Synthetic Peptide

<400> SEQUENCE: 49

Cys Pro Ala Asp Ala His Leu Gly Cys Ile Ser Tyr Cys
1               5                   10

<210> SEQ ID NO 50
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is tBuAla

<400> SEQUENCE: 50

Cys Ser Pro Asp Ala Tyr Leu Gly Cys Xaa Ser Tyr Cys
1               5                   10

<210> SEQ ID NO 51
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is C5g

<400> SEQUENCE: 51

Cys Ser Pro Asp Ala His Leu Gly Cys Xaa Ser Tyr Cys
1               5                   10

<210> SEQ ID NO 52
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is Cbg

<400> SEQUENCE: 52

Cys Ser Pro Asp Ala His Leu Gly Cys Xaa Ser Tyr Cys
1               5                   10

<210> SEQ ID NO 53
<211> LENGTH: 13
<212> TYPE: PRT
<213> ORGANISM: Artificial
<220> FEATURE:
<223> OTHER INFORMATION: Synthetic Peptide

<400> SEQUENCE: 53

Cys Ser Pro Asp Ala His Leu Ala Cys Ile Ser Tyr Cys
1               5                   10
```

```
<210> SEQ ID NO 54
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (7)..(7)
<223> OTHER INFORMATION: Xaa is Aib

<400> SEQUENCE: 54

Cys Ser Pro Asp Ala His Xaa Gly Cys Ile Ser Tyr Cys
1               5                   10

<210> SEQ ID NO 55
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is Cpg

<400> SEQUENCE: 55

Cys Ser Pro Asp Ala His Leu Gly Cys Xaa Ser Tyr Cys
1               5                   10

<210> SEQ ID NO 56
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (10)..(10)
<223> OTHER INFORMATION: Xaa is B-MeIle

<400> SEQUENCE: 56

Cys Ser Pro Asp Ala His Leu Gly Cys Xaa Ser Tyr Cys
1               5                   10

<210> SEQ ID NO 57
<211> LENGTH: 13
<212> TYPE: PRT
<213> ORGANISM: Artificial
<220> FEATURE:
<223> OTHER INFORMATION: Synthetic Peptide

<400> SEQUENCE: 57

Cys Ser Ala Asp Ala His Leu Gly Cys Ile Ser Tyr Cys
1               5                   10

<210> SEQ ID NO 58
<211> LENGTH: 13
<212> TYPE: PRT
<213> ORGANISM: Artificial
<220> FEATURE:
<223> OTHER INFORMATION: Synthetic Peptide

<400> SEQUENCE: 58

Cys Ser Pro Ala Ala His Leu Gly Cys Ile Ser Tyr Cys
1               5                   10

<210> SEQ ID NO 59
<211> LENGTH: 13
```

```
<212> TYPE: PRT
<213> ORGANISM: Artificial
<220> FEATURE:
<223> OTHER INFORMATION: Synthetic Peptide

<400> SEQUENCE: 59

Cys Ser Pro Asp Ala Ala Leu Gly Cys Ile Ser Tyr Cys
1               5                   10

<210> SEQ ID NO 60
<211> LENGTH: 13
<212> TYPE: PRT
<213> ORGANISM: Artificial
<220> FEATURE:
<223> OTHER INFORMATION: Synthetic Peptide

<400> SEQUENCE: 60

Cys Ser Pro Asp Ala His Ala Gly Cys Ile Ser Tyr Cys
1               5                   10

<210> SEQ ID NO 61
<211> LENGTH: 13
<212> TYPE: PRT
<213> ORGANISM: Artificial
<220> FEATURE:
<223> OTHER INFORMATION: Synthetic Peptide

<400> SEQUENCE: 61

Cys Ser Pro Asp Ala His Leu Ala Cys Ile Ser Tyr Cys
1               5                   10

<210> SEQ ID NO 62
<211> LENGTH: 13
<212> TYPE: PRT
<213> ORGANISM: Artificial
<220> FEATURE:
<223> OTHER INFORMATION: Synthetic Peptide

<400> SEQUENCE: 62

Cys Ser Pro Asp Ala His Leu Gly Cys Ala Ser Tyr Cys
1               5                   10

<210> SEQ ID NO 63
<211> LENGTH: 13
<212> TYPE: PRT
<213> ORGANISM: Artificial
<220> FEATURE:
<223> OTHER INFORMATION: Synthetic Peptide

<400> SEQUENCE: 63

Cys Ser Pro Asp Ala His Leu Gly Cys Ile Ala Tyr Cys
1               5                   10

<210> SEQ ID NO 64
<211> LENGTH: 13
<212> TYPE: PRT
<213> ORGANISM: Artificial
<220> FEATURE:
<223> OTHER INFORMATION: Synthetic Peptide

<400> SEQUENCE: 64

Cys Ser Pro Asp Ala His Leu Gly Cys Ile Ser Ala Cys
1               5                   10

<210> SEQ ID NO 65
<211> LENGTH: 13
<212> TYPE: PRT
```

<210> SEQ ID NO 65
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is K(N3)

<400> SEQUENCE: 65

Cys Xaa Pro Asp Ala His Leu Gly Cys Ile Ser Tyr Cys
1               5                   10

<210> SEQ ID NO 66
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (3)..(3)
<223> OTHER INFORMATION: Xaa is K(N3)

<400> SEQUENCE: 66

Cys Ser Xaa Asp Ala His Leu Gly Cys Ile Ser Tyr Cys
1               5                   10

<210> SEQ ID NO 67
<211> LENGTH: 13
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (5)..(5)
<223> OTHER INFORMATION: Xaa is K(N3)

<400> SEQUENCE: 67

Cys Ser Pro Asp Xaa His Leu Gly Cys Ile Ser Tyr Cys
1               5                   10